United States Patent
Koytiger

(10) Patent No.: US 11,942,223 B1
(45) Date of Patent: *Mar. 26, 2024

(54) SYSTEMS AND METHODS FOR RAPID GENE SET ENRICHMENT ANALYSIS

(71) Applicant: Immuneering Corporation, Cambridge, MA (US)

(72) Inventor: Grigoriy Koytiger, Cambridge, MA (US)

(73) Assignee: Immuneering Corporation, Cambridge, MA (US)

( * ) Notice: Subject to any disclaimer, the term of this patent is extended or adjusted under 35 U.S.C. 154(b) by 214 days.

This patent is subject to a terminal disclaimer.

(21) Appl. No.: 17/324,970

(22) Filed: May 19, 2021

Related U.S. Application Data

(63) Continuation of application No. 16/265,862, filed on Feb. 1, 2019, now Pat. No. 11,043,305.

(60) Provisional application No. 62/625,939, filed on Feb. 2, 2018.

(51) Int. Cl.
| | | |
|---|---|---|
| G16H 50/30 | (2018.01) | |
| G06F 17/15 | (2006.01) | |
| G16B 5/00 | (2019.01) | |
| G16B 20/00 | (2019.01) | |
| G16B 40/20 | (2019.01) | |
| G16B 50/20 | (2019.01) | |
| G16B 50/30 | (2019.01) | |

(52) U.S. Cl.
CPC ............ *G16H 50/30* (2018.01); *G06F 17/15* (2013.01); *G16B 5/00* (2019.02); *G16B 20/00* (2019.02); *G16B 40/20* (2019.02); *G16B 50/20* (2019.02); *G16B 50/30* (2019.02)

(58) Field of Classification Search
CPC ............ C12Q 1/6886; C12Q 2600/106; C12Q 2600/136; G01N 33/5023; G01H 50/30; G16B 5/00; G16B 5/30; G16B 50/20; G16B 20/00; G16B 40/20; G06F 17/15
USPC ........................................ 702/19, 20; 705/19
See application file for complete search history.

(56) References Cited

U.S. PATENT DOCUMENTS

| | | |
|---|---|---|
| 6,613,787 B2 | 9/2003 | Wilson et al. |
| 7,475,048 B2 | 1/2009 | Weston et al. |
| 7,805,388 B2 | 9/2010 | Weston et al. |
| 8,987,198 B2 | 3/2015 | Burow et al. |
| 9,309,564 B2 | 4/2016 | DePinho et al. |
| 9,945,862 B2 | 4/2018 | Funahashi et al. |
| 10,006,049 B2 | 6/2018 | Ling et al. |
| 10,676,791 B2 | 6/2020 | Moreaux et al. |
| 11,043,305 B1 | 6/2021 | Koytiger |

(Continued)

OTHER PUBLICATIONS

Alhamdoosh, M. et al., Easy and efficient ensemble gene set testing with EGSEA, F1000Research, 6:2010 (2017).

(Continued)

*Primary Examiner* — Andrew Joseph Rudy
(74) *Attorney, Agent, or Firm* — Choate, Hall & Stewart LLP; William R. Haulbrook; Samuel R. Polio

(57) ABSTRACT

Systems and methods for rapid gene set enrichment analysis and applications thereof are described. These systems and methods enable improved prioritization of relevant gene sets while maintaining a relatively lower false positive rate. Additionally, the ability to accelerate enrichment analysis and analyze hundreds of thousands of gene sets is described.

48 Claims, 16 Drawing Sheets

(56) References Cited

U.S. PATENT DOCUMENTS

| | | | |
|---|---|---|---|
| 2003/0073216 A1* | 4/2003 | Baker | C12N 5/06 |
| | | | 435/325 |
| 2006/0241015 A1 | 10/2006 | Sun et al. | |
| 2014/0079813 A1* | 3/2014 | Epstein | C12Q 1/6886 |
| | | | 435/6.12 |
| 2017/0342502 A1 | 11/2017 | Shull | |
| 2019/0316203 A1 | 10/2019 | Davison et al. | |

OTHER PUBLICATIONS

Barbie, D.A. et al., Systematic RNA interference reveals that oncogenic KRAS-driven cancers require TBK1, Nature, 462(7269):108-112 (2009).

Barry, W. T. et al., Significance analysis of functional categories in gene expression studies: a structured permutation approach, Bioinformatics, 21(9):1943-1949 (2005).

Beel, J., et al., Research-paper recommender systems: a literature survey, International Journal on Digital Libraries, 17(4):305-338 (2016).

Benjamini, Y. and Yekutieli, D., The control of the false discovery rate in multiple testing under dependency, The Annals of Statistics, 29(4):1165-1188 (2001).

Bouma, G., Normalized (pointwise) mutual information in collocation extraction, Proceedings of GSCL, 31-40 (2009).

Chen, E. Y. et al., Enrichr: interactive and collaborative HTML5 gene list enrichment analysis tool, BMC Bioinformatics, 14(1):128 (2013).

Cheng, J. and Yang, L., Comparing gene expression similarity metrics for connectivity map, IEEE International Conference on Bioinformatics and Biomedicine, pp. 165-170 (2013), [https://www.researchgate.net/publication/271556458_Comparing_gene_expression_similarity_metrics_for_connectivity_map] [retrieved on Mar. 1, 2019].

Cheng, J. et al., Systematic evaluation of connectivity map for disease indications, Genome medicine, 6:95, 8 pages (2014).

Church, K. W. and Hanks, P., Word Association Norms, Mutual Information, and Lexicography, Computational Linguistics, 16(1):22-29 (1990).

De Leeuw, C. A. et al., The statistical properties of gene-set analysis, Nature Review Genetics, 17:353-364, (2016) with Supplementary Information included (42 pages).

Dhillon, Sohita, Palbociclib: First Global Approval, Drugs, 75:543-551 (2015).

Duan, Q. et al., L1000CDS2: LINCS L1000 characteristic direction signatures search engine, Npj Systems Biology And Applications, 2:16015, 12 pages (2016).

Eli Lilly and Company, A Study in Participants with Acute Leukemia, 42 pages, (2010), [online] Clinical Trials Identifier: NCT01214603, from clinicaltrials.gov [retrieved on Mar. 1, 2019] [https://clinicaltrials.gov/ct2/show/study/NCT01214603].

Eli Lilly and Company, A Study of LY2090314 and Chemotherapy in Patients With Metastatic Pancreatic Cancer, 29 pages, (2012), [online] [https://clinicaltrials.gov/ct2/show/study/NCT01632306] Clinical Trials Identifier: NCT01632306, from clinicaltrials.gov [retrieved on Mar. 1, 2019].

Eli Lilly and Company, A Study of LY2090314 in Patients With Advanced or Metastatic Cancer, 26 pages, (2011), [online] Clinical Trials Identifier: NCT01287520, [https://clinicaltrials.gov/ct2/show/record/NCT01287520] [retrieved on Mar. 1, 2019].

Ferguson, L. B. et al., Genome-Wide Expression Profiles Drive Discovery of Novel Compounds that Reduce Binge Drinking in Mice, Neuropsychopharmacology, 43:1257-1266 (2017).

Fowler, K. D. et al., Leveraging existing data sets to generate new insights into Alzheimer's disease biology in specific patient subsets, Scientific Reports, 5:14324, 14 pages (2015).

Frazee, A. C. et al., ReCount: a multi-experiment resource of analysis-ready RNA-seq gene count datasets, BMC Bioinformatics, 12:449, 5 pages (2011).

Gaulton, A et al., ChEMBL: a large-scale bioactivity database for drug discovery, Nucleic Acids Research, 40(Database issue):D1100-D1107 (2012).

Gaulton, A. et al., The ChEMBL database in 2017, Nucleic Acids Research, 45(D1):D945-D954 (2017).

Goeman, J. J. et al., A global test for groups of genes: testing association with a clinical outcome, Bioinformatics, 20(1):93-99 (2004).

Hanzelmann, S. et al., GSVA: gene set variation analysis for microarray and RNA-seq data, BMC Bioinformatics, 14:7, 15 pages (2013).

Hermanto, U. et al., ErbB2-overexpressing human mammary carcinoma cells display an increased requirement for the phosphatidylinositol 3-kinase signaling pathway in anchorage-independent growth, Oncogene, 20:7551-7562 (2001).

Jiang, D. et al., Comprehensive Analysis of the Unfolded Protein Response in Breast Cancer Subtypes, JCO Precision Oncology, 1(1):1-9 (2017).

Jones, K. S., A statistical interpretation of term specificity and its application in retrieval, Journal of Documentation, 28(1):11-21 (1972).

Kanehisa, M. et al., KEGG: new perspectives on genomes, pathways, diseases and drugs, Nucleic Acids Research, 45(D1):D353-D361 (2017).

Keenan, A. B. et al., The Library of Integrated Network-Based Cellular Signatures NIH Program: System-Level Cataloging of Human Cells Response to Perturbations, Cell Systems Perspective, CellPress, 6:13-24, (2018).

Kelder, T. et al., WikiPathways: building research communities on biological pathways, Nucleic Acids Research, 40(Database issue):D1301-D1307 (2012).

Lachmann, A. et al., Massive Mining of Publicly Available RNA-seq Data from Human and Mouse, bioRxiv, 1:189092:1-9 (2017).

Lamb, J. et al., The Connectivity Map: Using Gene-Expression Signatures to Connect Small Molecules, Genes, and Disease, Science, 313(5795):1929-1935 (2006).

Law, C. W. et al., voom: Precision weights unlock linear model analysis tools for RNA-seq read counts, Genome Biology, 15(2):R29, 9 pages (2014).

Lee, E. et al., Inferring Pathway Activity toward Precise Disease Classification, PLOS Computational Biology, 4(11):e1000217, 9 pages (2008).

Lee, H. et al., Drug Repositioning for Cancer Therapy Based on Large-Scale Drug-Induced Transcriptional Signatures, PLoS ONE, 11(3):e0150460, 17 pages (2016).

Leydesdorff, L., Similarity measures, author cocitation analysis, and information theory, Journal of the American Society for Information Science and Technology, 56(7):769-772 (2005).

Liang, W. S. et al., Alzheimer's disease is associated with reduced expression of energy metabolism genes in posterior cingulate neurons, PNAS, 105(11):4441-4446 (2008).

Luo, W. et al., GAGE: generally applicable gene set enrichment for pathway analysis, BMC Bioinformatics, 10(161), 17 pages (2009).

Ma, J. et al., Appearance frequency modulated gene set enrichment testing, BMC Bioinformatics, 12:81, 9 pages (2011).

Owens, M. A. et al., HER2 Amplification Ratios by Fluorescence In Situ Hybridization and Correlation with Immunohistochemistry in a Cohort of 6556 Breast Cancer Tissues, Clinical Breast Cancer, 5(1):63-69 (2004).

Paik, H. et al., Integrating Clinical Phenotype and Gene Expression Data to Prioritize Novel Drug Uses, CPT: Pharmacometrics & Systems Pharmacology, 5(11):599-607 (2016).

Ritchie, M. E. et al., limma powers differential expression analyses for RNA-sequencing and microarray studies, Nucleic Acids Research, 43(7):e47, 13 pages (2015).

Salton, G et al., A Vector Space Model for Automatic Indexing, Communications of the ACM, 18(11):613-620 (1975).

San Lucas, F. A. et al., Cancer in silico drug discovery: a systems biology tool for identifying candidate drugs to target specific molecular tumor subtypes, Molecular Cancer Therapeutics, 13(12):3230-3240 (2014).

Santa-Maria, C.A. et al., A pilot study of palbociclib in patients with HER2-positive breast cancer with brain metastasis, Journal of

(56) References Cited

OTHER PUBLICATIONS

Clinical Oncology, 35(15 suppl):TPS1110-TPS1110 (2017) [retrieved: Mar. 11, 2019 6:49:44PM] http://ascopubs.org/doi/abs/10.1200/JCO.2017.35.15_suppl.TPS1110.

Schaefer, C. F. et al., PID: the Pathway Interaction Database, Nucleic Acids Research, 37:D674-D679, (2009).

Schaefer, G. et al., Erlotinib Directly Inhibits HER2 Kinase Activation and Downstream Signaling Events in Intact Cells Lacking Epidermal Growth Factor Receptor Expression, Cancer Research, 67(3):1228-1238 (2007).

Serguschichev, A., An algorithm for fast preranked gene set enrichment analysis using cumulative statistic calculation, bioRxiv, 1:060012, 9 pages (2016).

Spruill, M., Asymptotic Distribution of Coordinates on High Dimensional Spheres, Electronic Communications in Probability, 12:234-247 (2007).

Subramanian, A. et al., A Next Generation Connectivity Map: L1000 Platform and the First 1,000,000 Profiles, Cell, 171(6):1437-1452.e17 (2017).

Subramanian, A. et al., Gene set enrichment analysis: a knowledge-based approach for interpreting genome-wide expression profiles, PNAS, 102(43):15545-15550 (2005).

Tarca, A. L. et al., A comparison of gene set analysis methods in terms of sensitivity, prioritization and specificity, PloS one, 8(11):e79217, 10 pages (2013).

Tarca, A. L. et al., Down-weighting overlapping genes improves gene set analysis, BMC Bioinformatics, 13:136, 14 pages (2012).

Tavazoie, S. et al., Systematic determination of genetic network architecture, Nature Genetics, 22:281-285 (1999).

Tomfohr, J. et al., Pathway level analysis of gene expression using singular value decomposition, BMC Bioinformatics, 6(1):225, 11 pages (2005).

Wilkinson, M. D. et al., Comment: The FAIR Guiding Principles for scientific data management and stewardship, Scientific Data, 3:160018, 9 pages (2016).

Wu, D. and Smyth, G. K., Camera: a competitive gene set test accounting for inter-gene correlation, Nucleic Acids Research, 40(17):e133, 12 pages (2012).

Wu, D. et al., ROAST: rotation gene set tests for complex microarray experiments, Bioinformatics (Oxford, England), 26(17):2176-2182 (2010).

\* cited by examiner

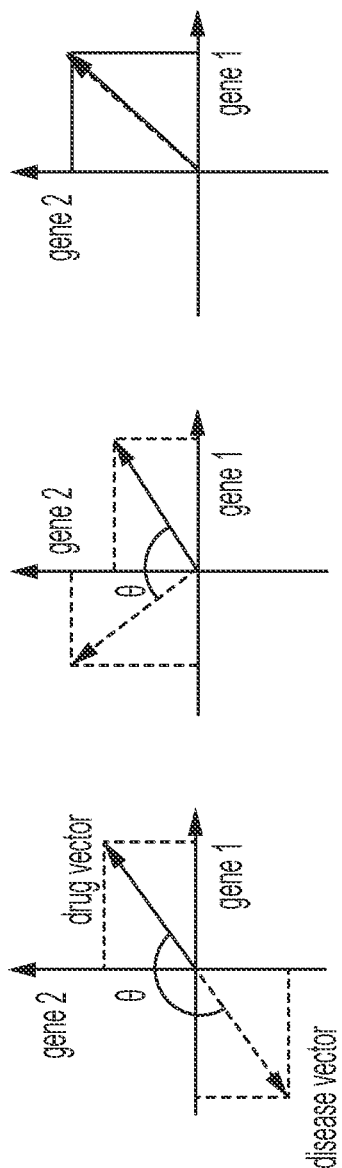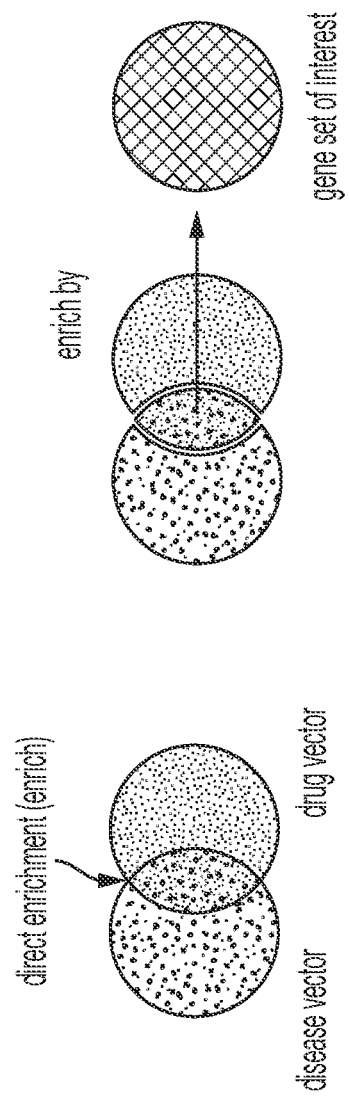

SYSTEMS AND METHODS FOR RAPID GENE SET ENRICHMENT ANALYSIS

CROSS REFERENCE TO RELATED APPLICATIONS

This application is a continuation of U.S. application Ser. No. 16/265,862, filed on Feb. 1, 2019, which claims priority to and benefit of U.S. Provisional Application No. 62/625,939, filed Feb. 2, 2018, the content of which is hereby incorporated herein by reference in its entirety.

FIELD OF THE INVENTION

The field of gene set analysis is a powerful approach that enables researchers to interpret their results within a broader biological context. Identification of enriched sets of genes can thus assist with translating and evaluating experimental results, mining existing datasets to derive information, and generating hypotheses for further studies.

BACKGROUND

Enrichment analysis for genes is a powerful tool to interpret lists of genes resulting from genomic, transcriptomic, or other genome-wide experiments. Enrichment analysis proceeds by defining a query gene set, also termed a "gene list," and testing for overlap against a library of "gene sets", also termed a "corpus". Gene sets are groupings of functionally related genes, often derived from expert curation of targeted biological experiments and collated in resources such as KEGG, PDI, and Gene Ontology databases. However, recent quantitative genome-wide experiments, such as those catalogued in the ENCODE, LINCS, Recount, and ARCHS4 databases, compose an increasing fraction of newly defined gene sets.

The theory of sets that underpins current analysis of gene set algorithms is typically binary, and thus not ideal for the newer classes of quantitative gene sets. For example, creating a discrete gene set from the result of a differential gene expression analysis requires splitting the results into an up and down regulated gene set, as well as equally weighting each gene regardless of the relative statistical significance based on results of the transcriptomic, genomic, or other genome wide experiment. This inefficiency wastes relevant data by diluting the signal and thus reduces the power of the enrichment analysis. Algorithms including Gene Set Enrichment Analysis (GSEA) and Enrichr partially mitigate this problem by allowing weights on the query gene list but not the gene set corpus.

Thus, there is a need for computationally efficient methods that take into account the quantitative nature of both query gene list and gene set that are better suited to deal with increasingly prevalent quantitative data types.

SUMMARY

Presented herein are systems, methods, and architectures related to gene set enrichment analysis. In certain embodiments, the methods and systems described herein compute per-gene enrichment statistics and use those statistics for another round of enrichment to identify drug mechanism. This extra layer of analysis is often helpful for the interpretation and planning of follow up experiments. Furthermore, in certain embodiments, the methods and systems described herein use sparse matrix linear algebra to represent and analyze lists of genes. The use of sparse matrices significantly improves computational efficiency, allowing for the analysis of large drug datasets.

Gene set analysis enables interpretation of biological measurements within a broader biological context. However, the binary nature of many gene sets that underlies the majority of current set enrichment is insufficient to fully analyze the recent explosion of quantitative genome-wide experiments. One embodiment of the claimed subject matter is Cosiner™, an R package that uses cosine similarity to identify enriched sets of genes. The results described herein demonstrate the ability of Cosiner™ to better prioritize relevant gene sets while maintaining a lower false positive rate than currently available tools. Moreover, Cosiner™ utilizes sparse matrix linear algebra to accelerate enrichment analysis, scaling to hundreds of thousands of gene sets. Leveraging the ability to analyze many sets at a high speed, Cosiner™ was used to analyze the large Library of Integrated Network-Based Cellular Signatures (LINCS) database to identify therapeutics for HER2+ breast cancer.

In one aspect, the invention is directed to a system for identifying one or more candidate therapies for treatment of a disease, the system comprising: a processor; and a memory having instructions stored thereon, wherein the instructions, when executed by the processor, cause the processor to: (a) identify a first gene set corresponding to the disease, wherein the first gene set is represented as a first numeric vector; (b) for each of a plurality of therapies: (i) identify a second gene set corresponding to the candidate therapy, wherein the second gene set is represented as a second numeric vector; and (ii) determine a measure of similarity between the first gene set and the second gene set using the first numeric vector and the second numeric vector; and (c) identify one or more members of the plurality of therapies that are candidates for treatment of the disease based on the measures of similarity.

In certain embodiments, the disease is cancer.

In certain embodiments, each of the plurality of therapies comprises a drug or a combination of drugs.

In certain embodiments, at least one of the plurality of therapies comprises a schedule (e.g., times and/or dosages) for administering (i) the drug or (ii) one or more drugs of the combination of drugs.

In certain embodiments, the measure of similarity between the first gene set and the second gene set using the first numeric vector and the second numeric vector quantifies a distance between the first numeric vector and the second numeric vector.

In certain embodiments, the measure of similarity between the first gene set and the second gene set using the first numeric vector and the second numeric vector quantifies a cosine similarity for the first numeric vector and the second numeric vector.

In certain embodiments, the measure of similarity between the first gene set and the second gene set using the first numeric vector and the second numeric vector comprises a use of sparse matrix linear algebra.

In certain embodiments, step (c) comprises generating a ranking based on the measures of similarity. In certain embodiments, the ranking based on the measures of similarity comprises a numerical ordering of the measures of similarity. In certain embodiments, the ranking comprises a range of the measures of similarity (e.g., the bottom 5% of similarities, e.g., the bottom 50% of similarities, e.g., the top 5% of similarities, e.g., similarities in the range of 0 to −1 cosine similarity). In certain embodiments, the ranking comprises identifying one or more groups of related therapies [e.g., based on one or more shared features (e.g., drug names and/or types, times of dosing, dosages, and combinations thereof)]. In certain embodiments, the group of related therapies is assigned a similarity value based on the similarity values of the members of the group (e.g., maximum similarity, e.g., minimum similarity, e.g., mean similarity, e.g., median similarity).

In certain embodiments, the instructions, when executed by the processor, further cause the processor to: (d) compute per-gene enrichment statistics and use the per-gene enrichment statistics to identify a drug mechanism. In certain embodiments, the instructions, when executed by the processor, cause the processor to use the per-gene enrichment statistics to identify a gene set of interest that is enriched within weighted overlap genes. In certain embodiments, the weighted overlap genes are weighted by their partial cosines.

In another aspect, the invention is directed to a system for analyzing lists of genes, the system comprising: a processor; and a memory having instructions stored thereon, wherein the instructions, when executed by the processor, cause the processor to: (a) represent each of a plurality of gene sets with a numerical vector: and (b) analyze the plurality of gene sets using sparse matrix linear algebra.

In certain embodiments, the instructions, when executed by the processor, cause the processor to compute a cosine similarity for a first numeric vector and a second numeric vector corresponding, respectively, to a first and second gene set from the plurality of gene sets using sparse matrix linear algebra.

In another aspect, the invention is directed to a system for identifying a drug mechanism, the system comprising: a processor; and a memory having instructions stored thereon, wherein the instructions, when executed by the processor, cause the processor to: (a) represent each of a plurality of gene sets with a numerical vector: (b) computing per-gene enrichment statistics from at least a subset of the numerical vectors; and (c) using the per-gene enrichment statistics to identify the drug mechanism.

In another aspect, the invention is directed to a method for identifying one or more candidate therapies for treatment of a disease, the method comprising: (a) identifying, by a processor of a computing device, a first gene set corresponding to the disease, wherein the first gene set is represented as a first numeric vector; (b) for each of a plurality of therapies: (i) identifying, by the processor, a second gene set corresponding to each of the one or more candidate therapies, wherein the second gene set is represented as a second numeric vector; and (ii) determining, by the processor, a measure of similarity between the first gene set and the second gene set using the first numeric vector and the second numeric vector, and (c) identifying, by the processor, one or more members of the plurality of therapies that are candidates for treatment of the disease based on the measures of similarity.

In certain embodiments, each of the plurality of therapies comprises a drug or a combination of drugs.

In certain embodiments, at least one of the plurality of therapies comprises a schedule (e.g., times and/or dosages) for administering (i) the drug or (ii) one or more drugs of the combination of drugs.

In certain embodiments, the disease is cancer.

In certain embodiments, the measure of similarity between the first gene set and the second gene set using the first numeric vector and the second numeric vector quantifies a distance between the first numeric vector and the second numeric vector.

In certain embodiments, the measure of similarity between the first gene set and the second gene set using the first numeric vector and the second numeric vector quantifies a cosine similarity for the first numeric vector and the second numeric vector.

In certain embodiments, the measure of similarity between the first gene set and the second gene set using the first numeric vector and the second numeric vector comprises a use of sparse matrix linear algebra.

In certain embodiments, step (c) comprises generating a ranking based on the measures of similarity. In certain embodiments, the ranking based on the measures of similarity comprises a numerical ordering of the measures of similarity. In certain embodiments, the ranking comprises a range of the measures of similarity (e.g., the bottom 5% of similarities, e.g., the bottom 50% of similarities, e.g., the top 5% of similarities, e.g., similarities in the range of 0 to −1 cosine similarity). In certain embodiments, the ranking comprises identifying one or more groups of related therapies [e.g., based on one or more shared features (e.g., drug names and/or types, times of dosing, dosages, and combinations thereof)].

In certain embodiments, the groups of subsets of the plurality of therapies is assigned a similarity value based on the similarity values of the members of the group (e.g., maximum similarity, e.g., minimum similarity, e.g., mean similarity, e.g., median similarity).

In certain embodiments, the method further comprises: (d) computing, by the processor, per-gene enrichment statistics and using, by the processor, the per-gene enrichment statistics to identify a drug mechanism. In certain embodiments, the method comprises using the per-gene enrichment statistics that identify the drug mechanism to plan follow-up experiments. In certain embodiments, the method comprises using the per-gene enrichment statistics that identify the drug mechanism to identify key genes driving overall enrichment. In certain embodiments the method comprises using the per-gene enrichment statistics that identify the drug mechanism to identify a gene set of interest enriched within weighted overlap genes. In certain embodiments, the weighted overlap genes are weighted by their partial cosines.

In another aspect, the invention is directed to a method for analyzing lists of genes, the method comprising: (a) representing, by a processor of a computing device, each of a plurality of gene sets with a numerical vector; and (b) analyzing, by the processor, the plurality of gene sets using sparse matrix linear algebra.

In certain embodiments, step (b) comprises computing a cosine similarity for a first numeric vector and a second numeric vector corresponding, respectively, to a first and second gene set from the plurality of gene sets.

In another aspect, the invention is directed to a method for identifying a drug mechanism, the method comprising: (a) representing, by a processor of a computing device, each of a plurality of gene sets with a numerical vector; (b) computing, by the processor, per-gene enrichment statistics from at least a subset of the numerical vectors; and (c) using, by the processor, the per-gene enrichment statistics to identify the drug mechanism.

Elements of embodiments involving one aspect of the invention (e.g., methods) can be applied in embodiments involving other aspects of the invention (e.g., compositions), and vice versa.

Definitions

In order for the present disclosure to be more readily understood, certain terms are first defined below. Additional definitions for the following terms and other terms are set forth throughout the specification.

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art.

Administration: As used herein, the term "administration" typically refers to the administration of a composition to a subject or system. Those of ordinary skill in the art will be aware of a variety of routes that may, in appropriate circumstances, be utilized for administration to a subject, for example a human. For example, in some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time.

Cancer: The terms "cancer", "tumor", and "carcinoma", are used herein to refer to cells that exhibit relatively abnormal, uncontrolled, and/or autonomous growth, so that they exhibit an aberrant growth phenotype characterized by a significant loss of control of cell proliferation. In some embodiments, a tumor may be or comprise cells that are precancerous (e.g., benign), malignant, pre-metastatic, metastatic, and/or non-metastatic. The present disclosure specifically identifies certain cancers to which its teachings may be particularly relevant. In some embodiments, a relevant cancer may be characterized by a solid tumor. In some embodiments, a relevant cancer may be characterized by a hematologic tumor. In general, examples of different types of cancers known in the art include, for example, hematopoietic cancers including leukemias, lymphomas (Hodgkin's and non-Hodgkin's), myelomas and myeloproliferative disorders; sarcomas, melanomas, adenomas, carcinomas of solid tissue, squamous cell carcinomas of the mouth, throat, larynx, and lung, liver cancer, genitourinary cancers such as prostate, cervical, bladder, uterine, and endometrial cancer and renal cell carcinomas, bone cancer, pancreatic cancer, skin cancer, cutaneous or intraocular melanoma, cancer of the endocrine system, cancer of the thyroid gland, cancer of the parathyroid gland, head and neck cancers, breast cancer, gastro-intestinal cancers and nervous system cancers, benign lesions such as papillomas, and the like.

Dosage: Those skilled in the art will appreciate that the term "dosage" may be used to refer to a physically discrete unit of an active agent (e.g., a therapeutic or diagnostic agent) for administration to a subject. Typically, each such unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen).

Gene: As used herein, the term "gene" refers to a DNA sequence in a chromosome that codes for a product (e.g., an RNA product and/or a polypeptide product). In some embodiments, a gene includes coding sequence (i.e., sequence that encodes a particular product): in some embodiments, a gene includes non-coding sequence. In some particular embodiments, a gene may include both coding (e.g., exonic) and non-coding (e.g., intronic) sequences. In some embodiments, a gene may include one or more regulatory elements that, for example, may control or impact one or more aspects of gene expression (e.g., cell-type-specific expression, inducible expression, etc.).

Gene Set: As used herein, the term "gene set" is used interchangeably herein with the term "gene list". Gene sets are groupings of gene representations (e.g., listings of genes) corresponding to genes with similar functions, e.g., participating in a defined signaling pathway, e.g., defined by their ontology). A gene set or list may be represented alphanumerically (e.g., as a numerical vector, e.g., as a matrix).

Gene Corpus: As used herein, the term "gene corpus" is a collection of gene sets, with each set within the collection having a unique identity. A gene corpus may be represented alphanumerically (e.g., as a matrix).

Genome: As used herein, the term "genome" refers to the total genetic information carried by an individual organism or cell, represented by the complete DNA sequences of its chromosomes.

Inhibitor: As used herein, the term "inhibitor" refers to an entity, condition, or event whose presence, level, or degree correlates with decreased level or activity of a target). In some embodiments, an inhibitor may be act directly (in which case it exerts its influence directly upon its target, for example by binding to the target); in some embodiments, an inhibitory agent may act indirectly (in which case it exerts its influence by interacting with and/or otherwise altering a regulator of the target, so that level and/or activity of the target is reduced). In some embodiments, an inhibitory agent is one whose presence or level correlates with a target level or activity that is reduced relative to a particular reference level or activity (e.g., that observed under appropriate reference conditions, such as presence of a known inhibitory agent, or absence of the inhibitory agent in question, etc).

Inhibiting tumor metastasis: As used herein, the phrase "inhibiting tumor metastasis" typically refers to a condition or event that correlates with decreased amount of tumor metastasis. In some embodiments, "inhibiting tumor metastasis" is synonymous with the phrase "treatment of tumor metastasis." In some embodiments, inhibiting tumor metastasis may include prevention or reduction of tumor metastasis. In some embodiments, inhibiting tumor metastasis may include prevention or reduction of tumor cell invasion. In some embodiments, inhibiting tumor metastasis may include prevention or reduction of lymph node metastases. In some embodiments, inhibiting tumor metastasis may include prevention or reduction of distant metastases. In some embodiments, inhibiting tumor metastasis may include increasing the timeframe during which a patient experiences or exhibits metastasis-free survival. In certain aspects, metastasis-free survival is defined as the time from initial administration of a therapeutic composition (e.g., an inhibitor of tumor metastasis) to the patient to the first detection of distant metastasis on imaging or death.

In vitro: As used herein, the term "in vitro" refers to events that occur in an artificial environment, e.g., in a test tube or reaction vessel, in cell culture, etc., rather than within a multi-cellular organism In vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Marker: A marker, as used herein, refers to an entity or moiety whose presence or level is a characteristic of a particular state or event. In some embodiments, presence or level of a particular marker may be characteristic of presence or stage of a disease, disorder, or condition. To give but one example, in some embodiments, the term refers to a gene expression product that is characteristic of a particular tumor, tumor subclass, stage of tumor, etc. Alternatively or additionally, in some embodiments, a presence or level of a particular marker correlates with activity (or activity level) of a particular signaling pathway, for example that may be characteristic of a particular class of tumors. The statistical significance of the presence or absence of a marker may vary depending upon the particular marker. In some embodiments, detection of a marker is highly specific in that it reflects a high probability that the tumor is of a particular subclass. Such specificity may come at the cost of sensitivity (i.e., a negative result may occur even if the tumor is a tumor that would be expected to express the marker). Conversely, markers with a high degree of sensitivity may be less specific that those with lower sensitivity. According to the present invention a useful marker need not distinguish tumors of a particular subclass with 100% accuracy.

Patient: As used herein, the term "patient" (or, as interchangeably used herein. "subject") refers to any organism to which a provided composition is or may be administered, e.g., for experimental, diagnostic, prophylactic, and/or therapeutic purposes. Typical patients include animals (e.g., mammals such as mice, rats, rabbits, non-human primates, and/or humans). In some embodiments, a patient is a human. In some embodiments, a patient is suffering from or susceptible to one or more disorders or conditions. In some embodiments, a patient displays one or more symptoms of a disorder or condition. In some embodiments, a patient has been diagnosed with one or more disorders or conditions. In some embodiments, the disorder or condition is or includes cancer, or presence of one or more tumors. In some embodiments, the disorder or condition is or includes metastasis of one or more tumors. In some embodiments, the patient is receiving or has received certain therapy to diagnose and/or to treat a disease, disorder, or condition.

BRIEF DESCRIPTION OF THE FIGURES

The foregoing and other objects, aspects, features, and advantages of the present disclosure will become more apparent and better understood by referring to the following description taken in conjunction with the accompanying drawings, in which:

FIG. 1A is a graph of a drug vector (solid arrow) and a disease vector (dotted arrow) that point in opposite directions (e.g., θ=180 degrees).

FIG. 1B is a graph of a drug vector and a disease vector that are at a right angle to each other (e.g., θ=90 degrees).

FIG. 1C is a graph of a drug vector and a disease vector that point perfectly in the same direction (e.g., θ=0 degrees).

FIG. 1D is a Venn Diagram of the operation of a direct enrichment of a gene set as performed by the function "enrich".

FIG. 1E is a Venn Diagram illustrating the operation of the "enrich by" function.

Figure 2A:
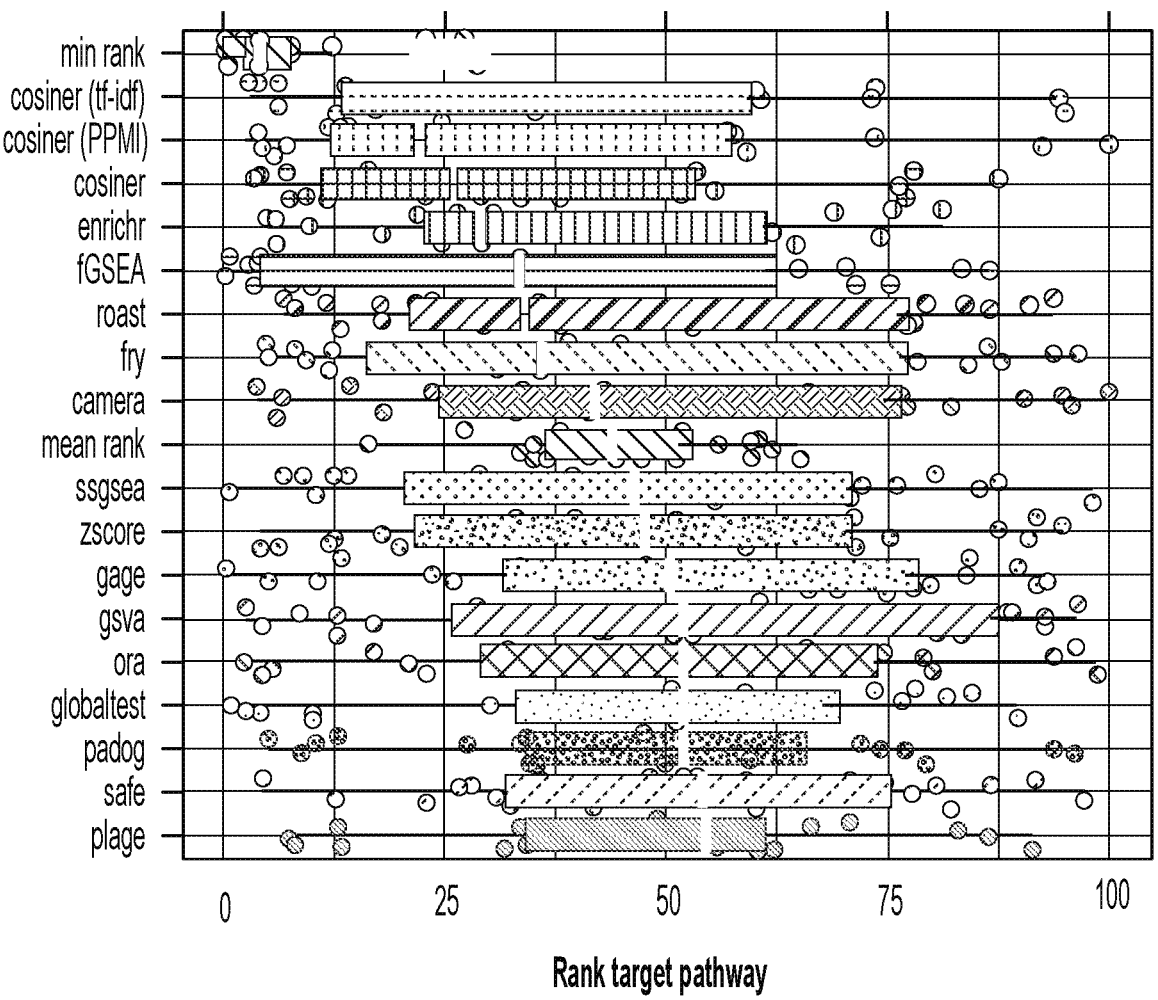
FIG. 2A is a graph depicting the prioritization of target KEGG pathways by different enrichment methods.

The features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements.

DETAILED DESCRIPTION

It is contemplated that systems, architectures, devices, methods, and processes of the claimed invention encompass variations and adaptations developed using information from the embodiments described herein. Adaptation and/or modification of the systems, architectures, devices, methods, and processes described herein may be performed, as contemplated by this description.

Throughout the description, where articles, devices, systems, and architectures are described as having, including, or comprising specific components, or where processes and methods are described as having, including, or comprising specific steps, it is contemplated that, additionally, there are articles, devices, systems, and architectures of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

Vector space models (VSM) provide a more appropriate mathematical underpinning for analyzing quantitative genome-wide experiments than other techniques. Instead of treating a collection of genes as a set, representing genes as a numeric vector enables the principled treatment of weights in both the query gene list and corpus of gene sets. This, for instance, allows for the inclusion of positive and negative weights arising from differential gene expression, single nucleotide polymorphism (SNP) effect sizes from GWAS analysis, or amplification size from copy number variation (CNV) analysis.

Cosiner™ is an R package that uses sparse matrices to compute a cosine similarity (cosSim) metric that quantifies gene overlap. Cosine similarity has been previously proposed as a metric to measure the distance between gene vectors. Cosine similarity can be thought of as the angle between two high dimensional gene vectors or a percent similarity normalized by vector magnitude. The values of cosSim range from −1 to 1 and its interpretation is analogous to Pearson correlation. In addition, Cosiner™ provides a per-gene enrichment statistic that provides the researcher with greater clarity into the key genes driving the overall enrichment. Furthermore, gene level scores are used by Cosiner™ to compute a secondary enrichment that allows the identification of relevant biological gene sets that can further aid the interpretation of enrichment results. Cosiner™ uses sparse matrices to represent gene sets and a non-permutation based statistical test, enabling rapid and efficient enrichment analysis even of many of the largest current gene set libraries.

Sparse Matrices can be Used to Represent Modern Genomic Data

A corpus of gene sets can be represented as a gene matrix, $C_1$. A row represents a gene 1 through n, a column a gene set 1 through s and each $g_{ij}$ a weight assigned to that gene as shown in Formula 1.

$$C_1 = \begin{bmatrix} g_{11} & \cdots & g_{1s} \\ \vdots & \ddots & \vdots \\ g_{n1} & \cdots & g_{ns} \end{bmatrix} \quad \text{Formula 1}$$

$C_1$ is a sparse matrix, given that only a small fraction of genes belong to a given gene set, that is, most $g_{ij}$ are zero.

Cosine Similarity Measures the Distance Between Two Vectors

Cosine similarity (cosSim) is a metric ranging from −1 to 1 that quantifies the cosine of the angle between two vectors of interest (e.g., in the simplified cases of FIGS. 1A to 1C) Q (query gene list) and S (gene set) as shown in Formula 2.

$$\text{similarity} = \cos\Theta = \frac{Q \cdot S}{\|Q\|_2 \cdot \|S\|_2} = \frac{\sum_{i=1}^{n} Q_i S_i}{\sqrt{\sum_{i=1}^{n} Q_i^2} \sqrt{\sum_{i=1}^{n} S_i^2}} \quad \text{Formula 2}$$

In order to better demonstrate the cosine similarity, a simplified model of a 2 gene system is presented herein. FIG. 1A shows drug and disease vectors that point in opposite directions (i.e., θ=180 degrees). The cosine similarity computed is equal to −1. This is interpreted to be reversal. Meaning, the disease and drug vector act in opposite manners on gene 1 and gene 2. If the drug and the disease vector point in exactly the same direction (FIG. 1C) (i.e., θ=0 degrees), the cosine similarity is 1. This instance is interpreted as mimicry. Meaning, the disease mimics the genetic signature of the drug, and vice versa. For the final case, there may be no apparent relationship between the drug and disease vectors. If the value for gene 2 is positive for both vectors whereas the values for gene 1 are of opposite sign, this results in θ=90 degrees and, therefore the cosine similarity is equal to 0. This is interpreted as orthogonality. A cosine similarity of 0 would indicate no meaningful relationship between the drug and disease vectors was found. With these relationships in mind, the cosine similarity may be extended to vectors with many more genes (e.g., a longer gene list) as the same mathematical underpinnings apply.

The overall cosine similarity is also defined as the summation of gene-wise scores normalized by the magnitude of the two vectors. Thus, it is possible to quantify the contribution of each gene to the overall cosine similarity, which is termed herein as the "partial cosine". Cosine similarity is closely related to the Pearson correlation metric. differing in only that the Pearson correlation subtracts the vector mean from each element thus breaking the sparsity of the matrix. For data whose mean is 0, the Pearson correlation and cosine similarity are equivalent.

Statistical Significance of Cosine Similarity Scores

If at least one of two gene lists being compared is centered around 0, the statistical significance of a cosine similarity (c) overlap follows an approximately normal distribution centered around 0 as stated by the central limit theorem. The variance of the distribution is the inverse of the dimensionality (n) of the gene set, more commonly referred to as the size of the gene universe. The background distribution is modeled using a t-distribution with n−2 degrees of freedom as shown in Formula 3.

$$t = \sqrt{\frac{n-2}{1-c^2}} \quad \text{Formula 3}$$

Cosiner™ enables testing of both one-sided and two-sided hypothesis tests. Multiple hypotheses testing is adjusted for using the Benjamini-Hochberg procedure.

tf-idf and PPMI Weighted Enrichments

Genes private to a given gene set provide better gene set prioritization compared to genes that are more widely shared and have multiple functions. Two weighing schemes are used to address this observation. The first is term frequency-inverse document frequency (tf-idf), which is defined as in Formula 4.

$$tf\text{-}idf(\text{gene, geneset}) = \left(\frac{1}{n_{\text{genes in geneset}}}\right) * \ln\left(\frac{n_{\text{genesets in corpus}}}{n_{\text{genesets containing a gene}}}\right) \quad \text{Formula 4}$$

The second weighting scheme uses the positive pointwise mutual information as seen in Formula 5.

$$PPMI(\text{gene, geneset}) = \max\left(\log_2\left(\frac{P(\text{gene, geneset})}{P(\text{gene})P(\text{geneset})}\right), 0\right) \quad \text{Formula 5}$$

Negative values are filtered out as they correspond to gene-gene set associations that are not different than what would be statistically expected.

Cosiner™ Provides Two Types of Enrichment Analysis

In the most simple enrichment analysis, Cosiner™ computes the cosine similarity between two gene vectors, representing two different molecular signatures. The approach is referred here to as a "direct enrichment" (FIG. 1D) and is performed by the function "enrich" in the Cosiner™ package.

Determining what biological functions are enriched in the overlap genes between query and gene set is often helpful for the interpretation and planning of follow up experiments. For example, this can occur when comparing a list of drug related genes to a list of disease related genes. The genes driving enrichment between a drug related list and a disease related list may fall into a pathway of interest. This second tier of analysis—termed "enrich by"—computes a secondary enrichment between the resulting overlap genes, weighted by their partial cosine and other gene sets of interest (FIG. 1E).

EXAMPLES

Example 1: Cosiner™ is a Fast Method with High Prioritization of Target Pathways and Low False Positive Rates To evaluate the performance of Cosiner™ against other methods, 24 microarray datasets from the KEGGdzPathwaysGEO package were used. The R package is incorporated herein by reference in its entirety. The KEGG pathway that matches the disease samples probed in each experiment defines a target pathway for each microarray experiment. The KEGG database is incorporated herein by reference in its entirety. The ability of Cosiner™ and other methods to highly rank the target pathways was tested. FIG. 2A displays the distribution of the percentile of the target pathways for each method when run according to the parameters described in the methods section. The plot shows the percent rank of the target pathways for 24 datasets for 18 methods, including three modalities of Cosiner™. Methods are sorted by the average target pathway ranking. For reference comparison, the combined minimum ranking across all methods (min rank) and the median ranking (mean rank) across all methods are plotted. Methods to the top more successfully prioritize the relevant KEGG gene set. Among the 15 methods compared, Cosiner™ and its embodiments consistently rank the target pathways highly especially when using tf-idf and PPMI weightings. Although not the first tool developed to address the gene set overlap issue, Cosiner™ substantially outperforms previous approaches such as the Pathway Analysis with Down-weighting of Overlapping Genes (PADOG) method.

Figure 3:
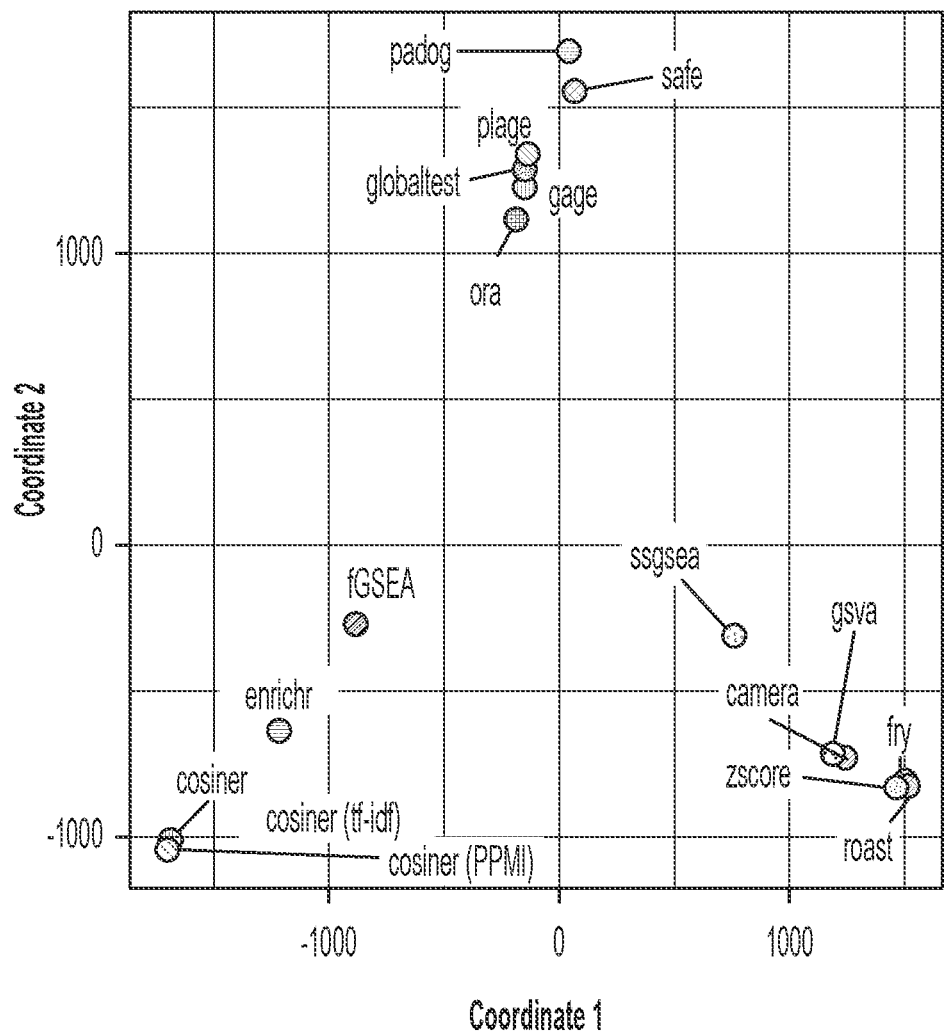
FIG. 3 is a multidimensional scaling (MDS) plot, which groups methods that result in similar enrichments close to each other.

All three modes of Cosiner™ (equal, tf-idf, and PPMI weighted) prioritize pathways similarly as visualized by the multidimensional scaling (MDS) plot generated of the pathway rankings (FIG. 3). The MDS plot shows that published algorithms fall into three distinct clusters, with similar enrichments being placed close to one another. Overall, three clusters appear. The embodiments of Cosiner™ are closely positioned with enrichr and fGSEA. A second cluster contains ssgsea, gsva, camera, zscore, roast and fry. The third cluster contains padog, safe, plage, globaltest, gage and ora.

Figure 2B:
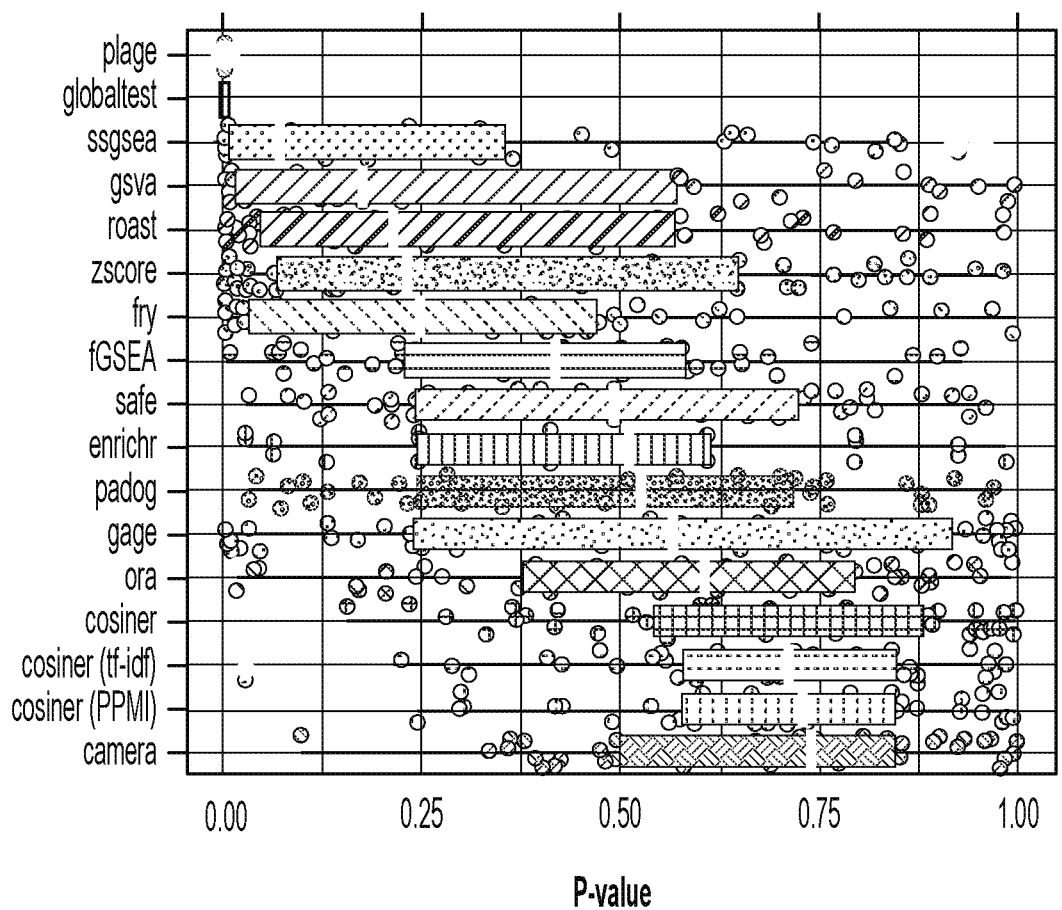
FIG. 2B is a graph showing the distribution of p-values of a target pathway for 50 instances of microarray dataset gene permutations.

To evaluate the false positives detected by the different enrichment methods, the gene IDs for a microarray sample (GSE5281_HIP) were permuted 50 times. Random shuffling of gene IDs in the microarray should yield no meaningful, significant enrichments of any target pathway. FIG. 2B shows the distribution of rankings for the target pathways in 50 datasets with permuted gene IDs. Methods to the bottom more often assign insignificant scores to permuted data. Camera most successfully assigns the most insignificant p-values to target pathways with the three modalities of Cosiner™ closely following. This result exhibits the ability of Cosiner™ to discriminate between real signal and noise in the data.

Figure 2C:
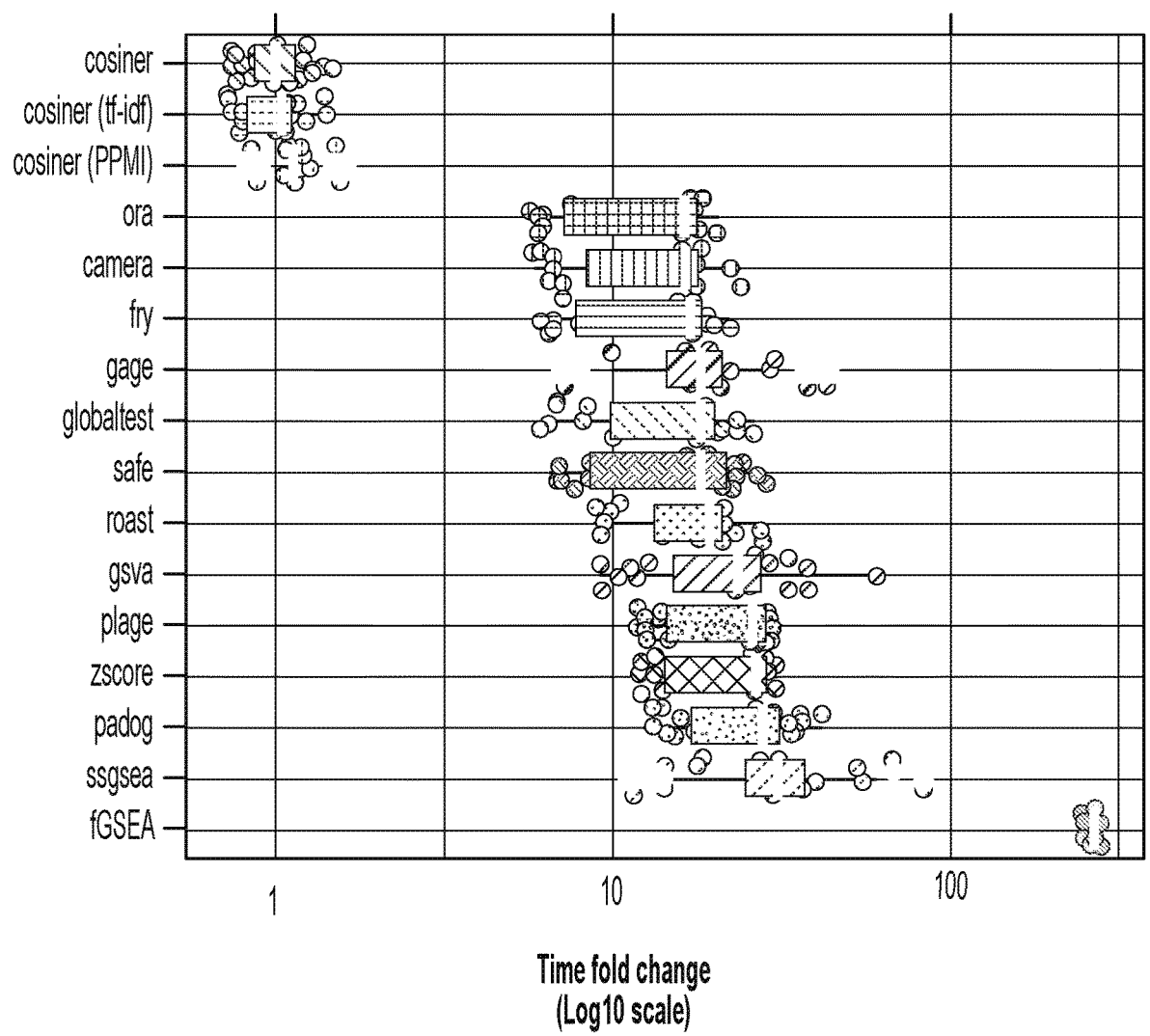
FIG. 2C is a graph showing speed tests for enrichment methods.

Cosiner™ uses sparse matrix linear algebra, which provides significant speed gains versus other methods. To assess the speed of each enrichment method, the enrichments from FIG. 2B were run using a single core. FIG. 2C displays the distribution of the running times for the 24 enrichments as a fold change from the running time of Cosiner™. Enrichr was not run as the algorithm does not run locally. Cosiner™ was the fastest algorithm by at least an order of magnitude and more than two orders of magnitude faster than the fGSEA algorithm.

Methods of Example 1

HER2+ Breast Cancer Signature

RNA-seq data from breast cancer The Cancer Genome Atlas (TCGA) samples were downloaded from https://gdac.broadinstitute.org. TCGA is incorporated herein by reference in its entirety. 40 tumor samples with clinically measured breast cancer markers HER2, estrogen (ER) and progesterone (PR) were fit with a limma model of gene expression. This model is then used to identify differentially expressed genes (DEGs) HER2+ and HER2 negative samples while correcting for ER and PR status. The HER2+ breast cancer signature is defined by the top 500 DEGs by p-value weighted by the limma moderated t-statistic.

Drug Enrichments of HER2+ Breast Cancer Signature

Drug signatures are generated from the LINCS Phase 2 dataset (GSE70138), which is incorporated herein by reference in its entirety. The compounds were mapped to the ChEMBL 22 database, which is incorporated herein by reference in its entirety, using a combination of name and INCHI keys and collapsed the Level 5 data across replicate experiments by averaging the reported gene level Z-statistics, restricting to the top 500 genes by absolute Z-statistic. Next, the resultant ~91,000 cell line specific drug signatures were evaluated for their ability to reverse the HER2+ signature per cosine similarity. To elucidate the biology of the HER2+ breast cancer signature, enrichments against the ARCHS4 kinase and transcription factor gene sets, NC cancer, and Wikipathways databases were run. These aforementioned databases are incorporated herein by reference in their entirety Prioritization of Target Pathways in Gold Standard Dataset To assess the quality of enrichment analysis, the evaluation scheme introduced by Tarca et al. (2013) was performed using the Bioconductor package KEGGdzPathwaysGEO, which is incorporated herein by reference in its entirety. The package contains 24 microarray experiments for diseases which match a pathway in the KEGG database. Limma was used to identify differentially expressed genes (DEGs) for each disease dataset which were then used to assess overlap with the KEGG corpus. For Cosiner™, the top 500 genes by p-value with weights corresponding to the moderated t-statistic output from limma were used. The effect of running Cosiner™ with equal, tf-idf, or PPMI weights on the gene set corpus was evaluated.

Enrichr was run using the enrichR package and the top 500 DEGs by p-value. fGSEA was run using the parameters: min_gs 10, max_gs 500, exponent 1, and nperm 1e+06. EGSEA package was used to run 12 enrichment methods that are used to compute the single score. The default parameters for EGSEA were used. The methods included by EGSEA are ora, globaltest, plage, safe, zscore, gage, ssgsea, padog, gsva, camera, roast, and fry. Methods were run following the work of Allhamdoosh et al. (2017) using gene sets defined in the most recent version of KEGG 2016, which is incorporated herein by reference in its entirety.

Example 2: Revealing the Biology of HER2+ Breast Cancer and Identification of Candidate Therapies To demonstrate a relevant use case of Cosiner™, Cosiner™ was used to identify candidate therapies for HER2+ breast cancer. An in silico gene expression signature of HER2+ breast cancer was built (see Example 1), and compared to the genetic signatures of known HER2+ and HER2− breast cancer cell lines using Cosiner™. Then, Cosiner™ was used to screen, in silico, cell line specific drug signatures against breast cancer cell line genetic signatures. The screen determined potential candidate therapies for the HER2+ cell line and identified key genetic mechanisms of action.

Study Results of Example 2

A HER2+ breast cancer gene expression signature was generated as described in the methods section of Example 1 (HER2+ Breast Cancer Signature), since the disease is relatively well characterized and thus can act as a positive control to assess algorithmic accuracy. The human epidermal growth factor receptor (HER2), also known as ErbB2, is part of the ErbB family of receptor tyrosine kinases and its amplification or overexpression of HER2 is found in about 15-20% of breast cancers.

One goal of the study was to identify biological functions enriched in the HER2+ breast cancer gene signature, the method of which was described in the Methods section of Example 1. Table 1 and 2 display the tf-idf weighted cosine similarities against the transcription (Table 1) and kinase (Table 2) gene sets from ARCHS4, which is incorporated herein by reference in its entirety. The top kinase enrichment corresponds to HER2 (ErbB2) itself.

TABLE 1

Kinases enriched for the HER2 signature.

| gene set | cosine similarity | p-value | adjusted p-value |
|---|---|---|---|
| ERBB2 | 9.6% | 2.9e−29 | 1.4e−26 |
| FGFR4 | 4.0% | 4.2e−06 | 1.0e−03 |
| RPS6KB1 | 3.8% | 9.7e−06 | 1.6e−03 |
| TNK2 | −3.7% | 1.9e−05 | 2.4e−03 |
| KSR1 | −3.2% | 2.3e−04 | 2.3e−02 |

TABLE 2

Transcription factors enriched for the HER2 signature.

| gene set | cosine similarity | p-value | adjusted p-value |
|---|---|---|---|
| BRD9 | 7.4% | 5.6e−21 | 9.5e−18 |
| TFAP2C | 6.5% | 1.9e−16 | 1.6e−13 |
| ESR1 | 5.0% | 3.3e−10 | 1.9e−07 |
| ZNF217 | 4.5% | 1.1e−08 | 4.5e−06 |
| SPDEF | 4.3% | 6.4e−08 | 2.2e−05 |
| FOXA1 | 4.1% | 2.1e−07 | 5.9e−05 |
| XBP1 | 4.0% | 3.7e−07 | 9.0e−05 |
| GATA3 | 3.7% | 2.2e−06 | 4.7e−04 |
| TRPS1 | 3.7% | 3.1e−06 | 5.9e−04 |
| GRHL2 | 3.4% | 1.9e−05 | 3.3e−03 |

When switching from tf-idf to equal weighting, the same HER2 kinase (ERBB2) enrichment decreases (Table 3). The transcription factors enriched include ESR1 and XBP1, which have been shown to play important roles in breast cancer (Fable 2). ER status was a covariate in the linear model generating the HER2+ Breast Cancer Signature, indicating that HER2 amplification itself is capable of driving ER signaling.

TABLE 3

Kinase enrichments for HER2 signature with different weighted cosine similarities.

| gene set | Similarity (tf-idf) | p_value (tf-idf) | p_adjust (tf-idf) | similarity (equal) | p_value (equal) | p_adjust (equal) |
|---|---|---|---|---|---|---|
| ERBB2 | 9.6% | 2.9e−29 | 1.4e−26 | 8.1% | 2.6e−21 | 1.3e−18 |
| FGFR4 | 4.0% | 4.2e−06 | 1.0e−03 | 4.0% | 2.6e−06 | 6.4e−04 |
| RPS6KB1 | 3.8% | 9.7e−06 | 1.6e−03 | 3.6% | 3.1e−05 | 5.1e−03 |
| TNK2 | −3.7% | 1.9e−05 | 2.4e−03 | −3.3% | 1.3e−04 | 1.6e−02 |
| KSR1 | −3.2% | 2.3e−04 | 2.3e−02 | −3.0% | 4.1e−04 | 4.0e−02 |

Figure 4:
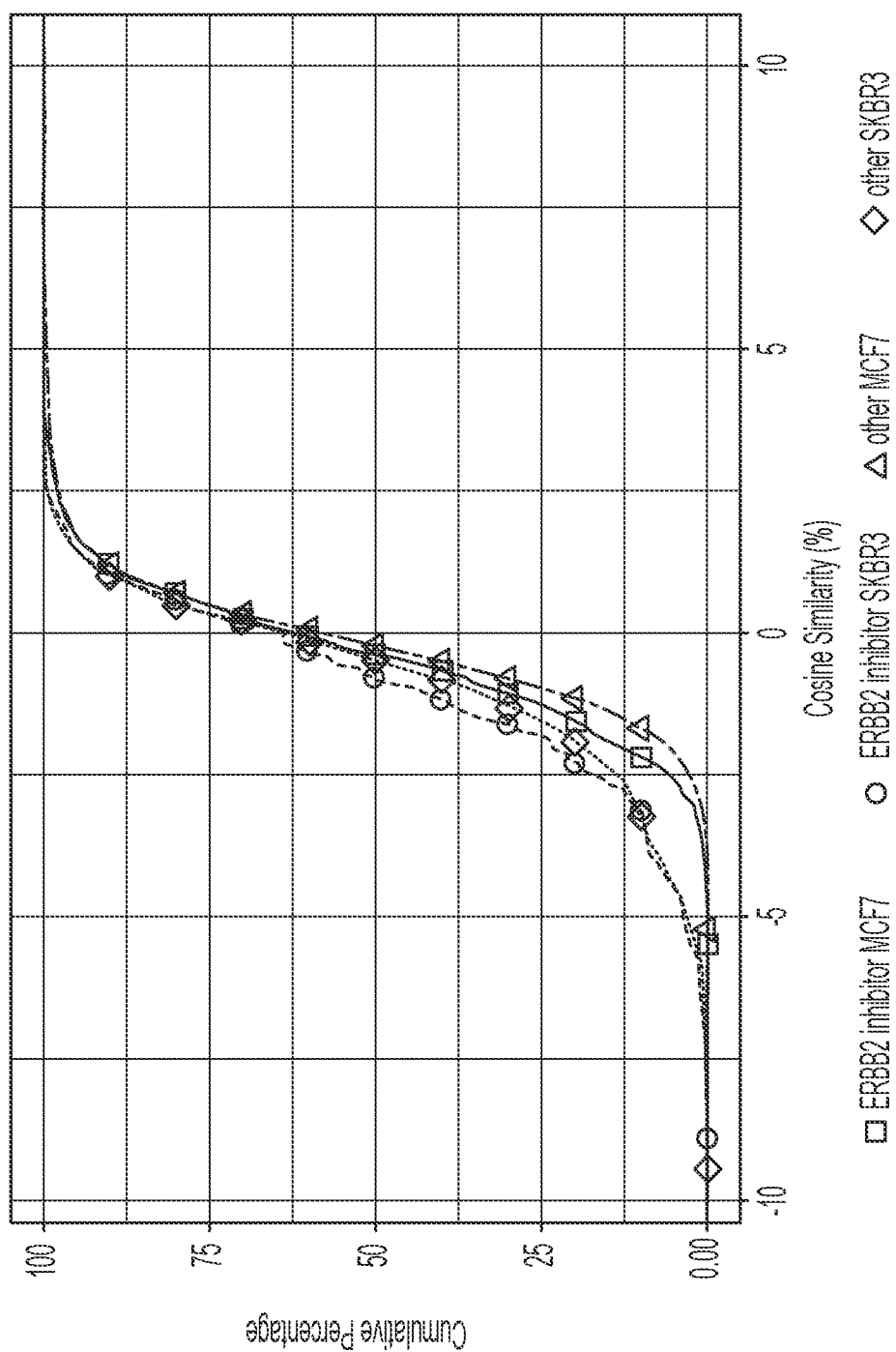
FIG. 4 is a graph of the Empirical Cumulative Distribution Function of cosine similarities—as a percent—between HER2+ disease gene expression signature and drugs profiled in the breast cancer cell lines SKBR3 and MCF7 in the LINCS dataset. For each cell line the distributions of drugs annotated within the ChEMBL database to directly target HER2 and all other drugs are plotted.

Cosiner™ was used to run an in silico screen of the HER2+ breast cancer signature against cell line specific LINCS drug signatures generated in two breast cancer cell lines, SKBR3 and MCF7. MCF7 is a HER2− breast cancer cell line, while SKBR3 is a HER2+ breast cancer cell line, which indicates that the gene expression signal of SKBR3 would be driven by HER2. To visualize how different classes of treatments are distributed for each cell line, the empirical cumulative density of the cosine similarity scores were plotted (FIG. 4). Most drug treatments for SKBR3 and MCF7 are centered around 0 cosine similarity, indicating they neither reverse nor mimic the disease signature. Without being bound to any theory, these treatments are unlikely to be treatments for breast cancer. HER2 (ErbB2) inhibitors are shown to have more negative cosine similarities ("ErbB2 inhibitor SKBR3") and therefore more successfully reverse the model disease cell line signature. In addition, this figure shows that most drugs identified as ErbB2 inhibitors do not as successfully reverse the signature of the HER2− breast cancer cell line, MCF7. Without wishing to be bound to any particular theory, this may be because the gene expression is not driven by HER2 gene in that cell line. In contrast, in the SKBR3 cell line, other drugs cause the reversal of HER2 gene expression, likely because the drugs modulate the HER2 pathway at nodes downstream of HER2. These drugs are thus capable of blocking HER2 driven gene expression without direct inhibition of HER2. This shows that Cosiner™ successfully identifies SKBR3 as the correct context to investigate HER2 therapies.

Figure 5A:
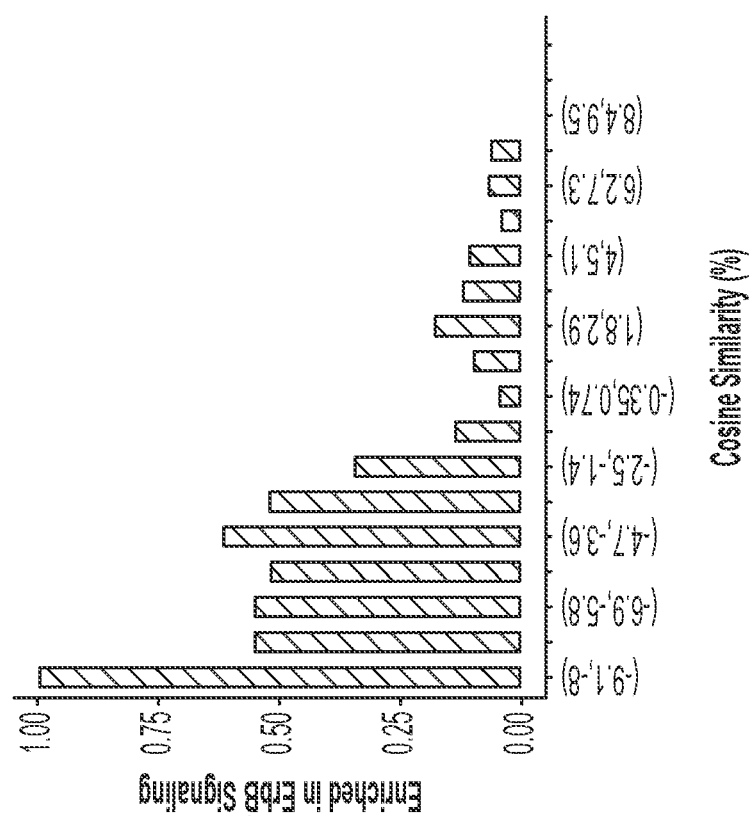
FIG. 5A is a histogram showing the fraction of the number of HER2+ inhibitor drugs at different intervals of cosine similarity between the drug and HER2+ breast cancer signatures.
Figure 5B:
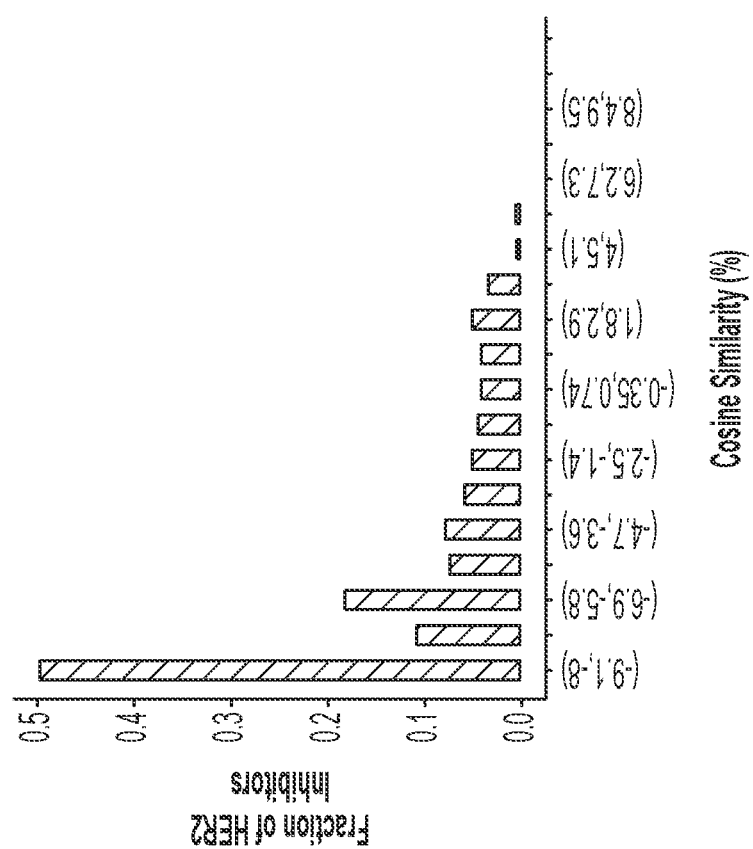
FIG. 5B is a graph showing the fraction of overlap genes at each cosine similarity interval that are enriched in ErbB pathway signaling for the histogram of 5A.

FIG. 5A shows the percent cosine similarities of HER2 inhibitor drug signatures to the in silico HER2+ breast cancer model. HER2 inhibitors are strongly enriched in the highest reversal (most negative) cosine similarity bins (FIG. 5B). These are true positive results as HER2 inhibitors are being used to treat HER2+ breast cancer. These results indicate that Cosiner™ is effective in generating novel drug hypotheses using only drug and disease gene expression data.

Figure 5D:
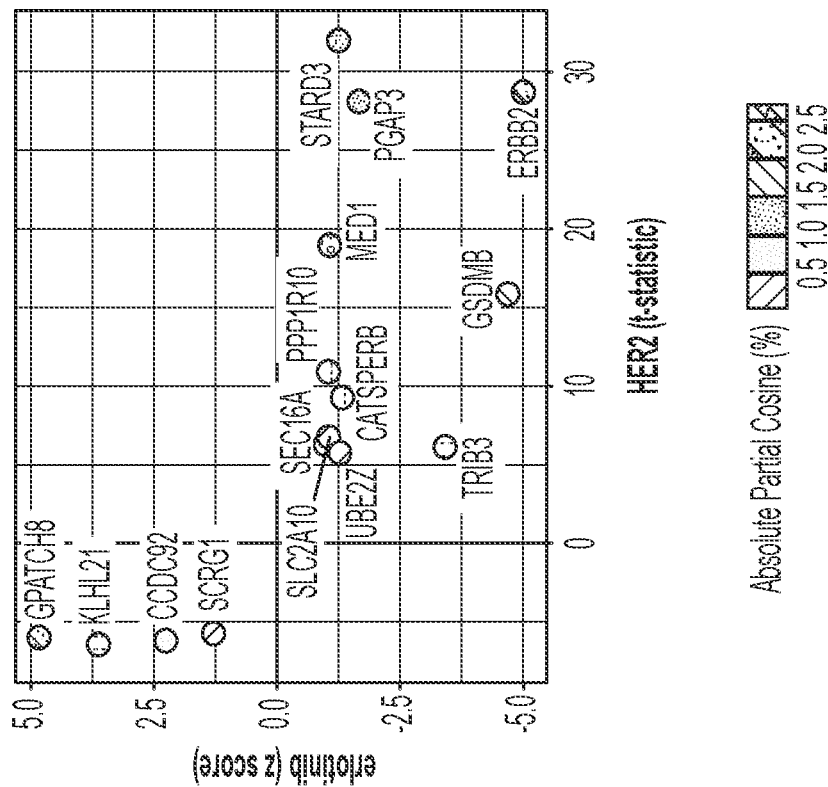
FIG. 5D is a scatter plot comparing moderated t-statistic of gene expression changes for HER2+ breast cancer and the average robust z-score of erlotinib induced gene expression changes in the SKBR3 cell line at 24 hours. The shaded scale shows the contribution of each gene to the cosine similarity.
Figure 5C:
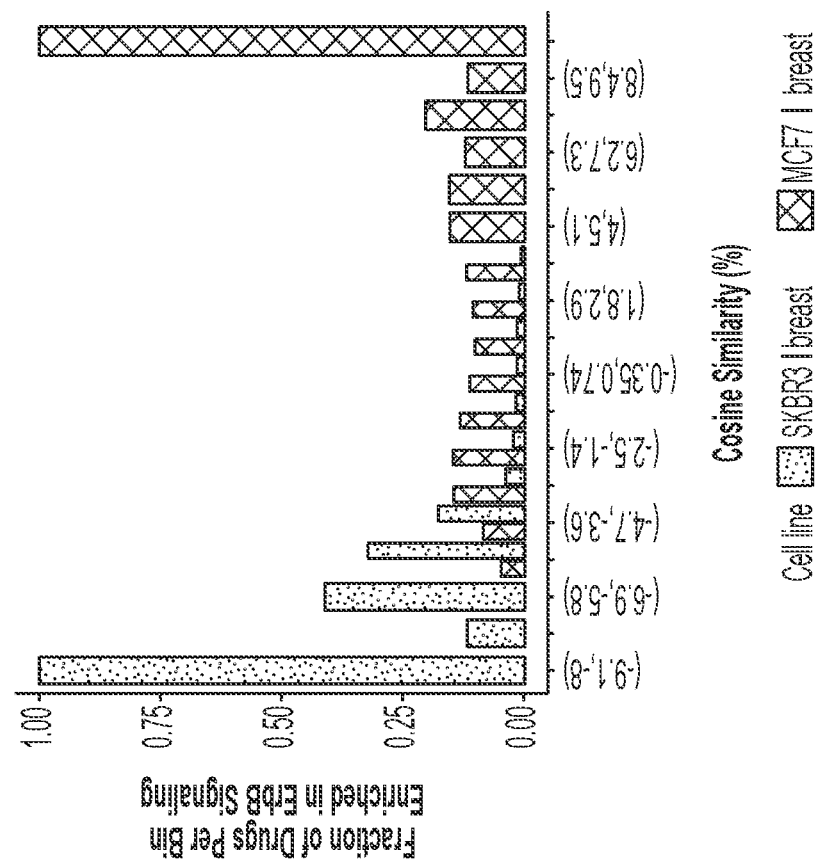
FIG. 5C is a graph showing the fraction of overlap genes between drug and breast cancer signatures (SKBR3 and MCF7) that are enriched in ErbB pathway signaling at different cosine intervals.
Figure 6:
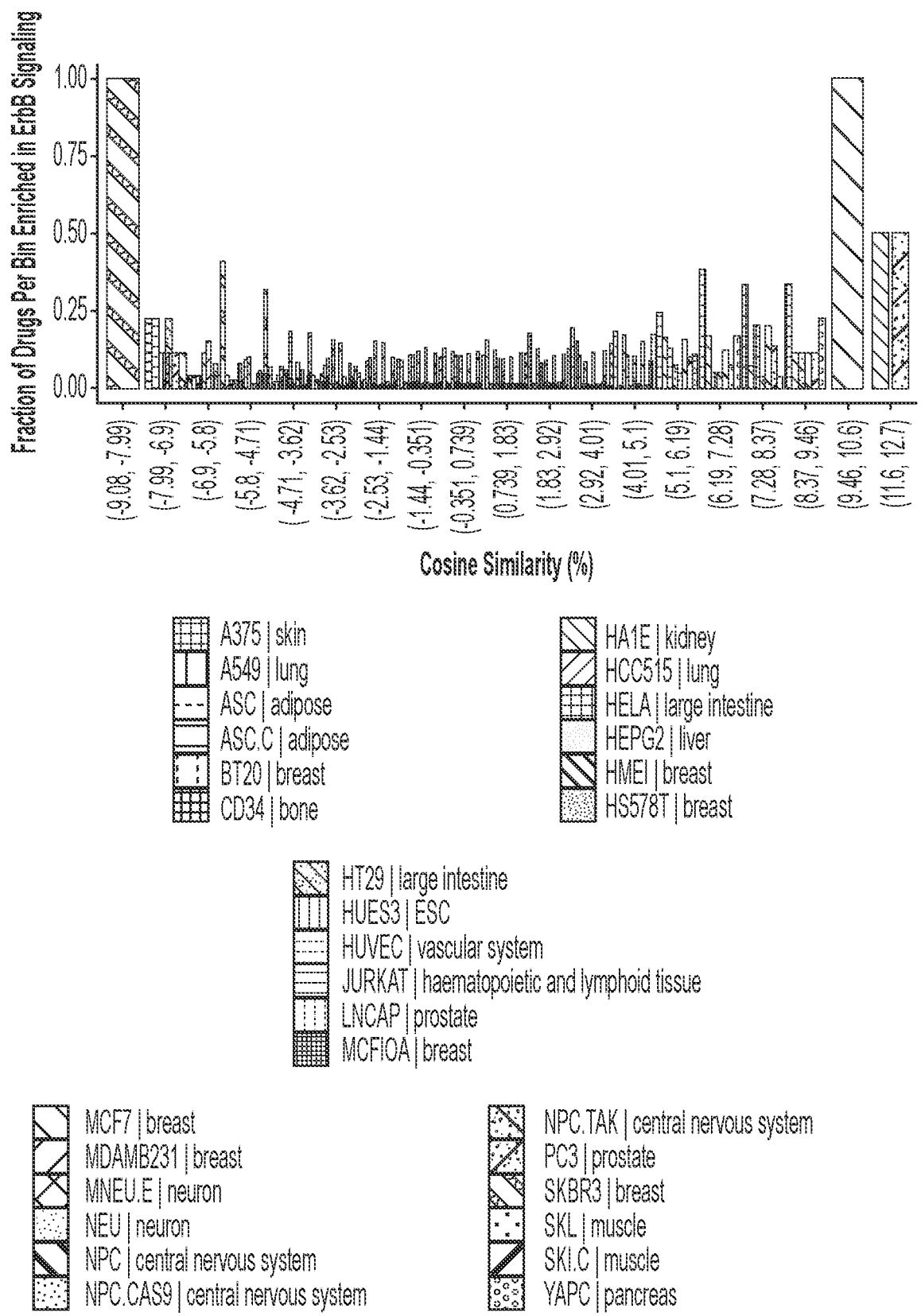
FIG. 6 is a graph of the fraction of overlap genes between drug and disease signatures at each cosine interval expressed as a percent that are enriched in ErbB signaling as defined by NCI Nature pathway. The distribution of 30 cell lines at different cosine similarity levels is shown.

How different breast cancer cell line types were distributed at different cosine similarity levels was also investigated (FIG. 5C). Interestingly, the number of drugs per bin enriched in ErbB signaling is the highest at the most negative cosine similarity levels for SKBR3. In contrast, the enrichment of ErbB is most prominent at the most positive cosine intervals for MCF7. Previously, the SKBR3 cell line has been shown to express HER2 kinase while the MCF7 cell line does not. To demonstrate the specificity of HER2 inhibitors to HER2+ cancer, the same analysis was carried out for other cell lines. FIG. 6 shows a total of 30 cell lines, including the aforementioned breast cancer cell lines MCF7 and SKBR3, investigated, again showing the fraction of overlap genes between drug and disease signatures that are enriched in ErbB signaling. The cell lines correspond to a wide diversity of cancer types from multiple tissues of origin. Without wishing to be bound to any theory, most cancer cell types do not show strong negative or positive cosine similarities, which corresponds to clinical knowledge that dysfunction is not a driving factor in these cancer types. Because the results are not uniformly strong, they imply that Cosiner™ is sensitive to cell line specific pathway activity, thus enabling it to prioritize cell line models for further drug hypothesis evaluation.

Overall, 528 drug signatures (at least one dose and time point) showed significant reversal (adjusted p-value<0.05) across any cell line. Table 4 details the top drug candidates that reverse the HER2+ breast cancer signature in the SKBR3 cell line. The top candidate palbociclib is approved for ER+HER2− breast cancer and, as of the writing of this manuscript, is undergoing trials for HER2+ breast cancer. The second highest ranked compound is erlotinib, an inhibitor of the epidermal growth factor receptor (EGFR) family of transmembrane tyrosine kinase growth factor receptors which includes HER2/ErbB2.

TABLE 4

Candidate therapies for HER2 signatures in SKBR3

| Drug Name | cosine similarity | Dose (μM) | Time (h) | adjusted p-value |
|---|---|---|---|---|
| palbociclib | −9.1% | 0.04 | 3 | 1.8e−18 |
| erlotinib | −8.5% | 0.04 | 24 | 2.9e−16 |
| linsitinib | −8.4% | 3.00 | 24 | 8.6e−16 |
| vemurafenib | −7.2% | 0.10 | 24 | 1.1e−11 |
| pilaralisib | −6.9% | 10.00 | 24 | 1.7e−10 |
| chembl3392893 | −6.5% | 0.04 | 24 | 3.0e−09 |
| afatinib | −6.5% | 0.10 | 3 | 3.5e−09 |
| bms-345541 | −6.4% | 0.40 | 3 | 4.8e−09 |
| chembl2178734 | −6.3% | 10.00 | 24 | 8.0e−09 |
| chembl2178734 | −6.3% | 3.00 | 24 | 1.4e−08 |

To shed light on the potential mechanisms of action of the LINCS drugs in HER2+ breast cancer, an "enrich by" analysis was run using the NCI-Nature 2016, ARCHS4 transcription factors and kinases, and WikiPathways 2016 databases. The databases are incorporated herein by reference in their entirety. Enriching the overlap genes for each drug signature against all pathways resulted in performing 261 million distinct enrichments in ~100 minutes, a number that is impractical for most other methods. FIG. 5B shows the distribution of drugs that enriched in the term "ErbB signaling" from the NCI-Nature database of expertly curated cancer pathways. Drugs with enrichments of "ErbB signaling" predominate among highest reversal bins by cosine similarity. 39 drugs are enriched in ErbB kinase signaling, yet do not list HER2 as a target in ChEMBL, which is incorporated herein by reference in its entirety. Without wishing to be bound to any theory, these drugs could function as potential HER2 inhibitors or modulate the HER2 pathway through other targets.

Examining the specific genes driving the cosine similarity score yields insights into Cosiner™ enrichment results. The partial cosine quantifies the contribution of each individual gene to overall reversal and thus can provide mechanistic insights and additional testable hypotheses for further experimental evaluation. Here, the described methodology was used to investigate the erlotinib drug enrichment which shows strong reversal of the HER2 signature, which is #2 overall in Table 4. FIG. 5D shows the drug vector weights as a function of the disease vector weights, and visualizes the strong anti-correlation between the two. The points, corresponding to individual genes, are shaded according to the resulting partial cosine, and ErbB2 has the highest contribution to overall reversal. Table 5 shows all the gene sets enriched for the overlap genes, weighted by their partial cosines, between the HER2+ signature and the erlotinib signature. The ErbB2 kinase signaling pathway is determined to be enriched across the ARCHS4 kinase, NCI-Nature 2016, and Wikipathways 2016 databases.

TABLE 5

Gene sets enriched in genes driving reversal of HER2+ signature by erlotinib.

| ARCHS4 kinases coexp | NCI Nature 2016 | Wikipathways 2016 |
|---|---|---|
| ERBB2_human_kinase_ARCHS4_coexpression (2.1le−10) | ErbB receptor signaling network_Homo sapiens_2c26d51f-6192-11e5-8ac5-06603eb7f303 (1.12e−17) | Bladder Cancer_Homo sapiens_WP2828 (6.44e−20) |
| FGFR4_human_kinase_ARCHS4_coexpression (8.1e−08) | ErbB2/ErbB3 signaling events_Homo sapiens_51e35311-6192-11e5-8ac5-06603eb7f303 (1.6e−11) | Extracellular vesicle-mediated signaling in recipient cells_Homo sapiens_WP2870 (6.4le−19) |
| | ErbB4 signaling events_Homo sapiens_6104ebb2-6192-11e5-8ac5-06603eb7f303 (1.44e−09) | ErbB signaling pathway_Mus musculus_WP1261 (1.le−14) |
| | | ErbB Signaling Pathway_Homo sapiens_WP673 (6.24e−13) |

Example 3: Cosiner™ can be Used to Screen Small Molecules to Identify Novel Therapeutic Candidates that Modulate the Genes Involved in Metastasis In order to demonstrate a use case of the Cosiner™ platform, this exemplified embodiment of Cosiner™ was used to search for small molecule inhibitors of metastasis to identify novel therapeutic candidates that modulate the genes involved in metastasis. These small molecule inhibitors were designated for further experimental analysis using an assay to assess the effectiveness of using Cosiner™ to predict the reversal of the metastatic phenotype of the designated cell lines.

Creation of the Metastatic Tumor Genetic Signature

The first step was determining a genetic signature of metastatic cancer. The primary tumor breast cancer RNA-Seq dataset from The Cancer Genome Atlas (TCGA) was processed. TCGA is incorporated herein by reference in its entirety. Primary tumors from patients with metastasis (lymph node metastasis) were compared to primary tumors from patients without metastasis (no lymph node metastasis and no recorded distant metastases) using differential expression. The net result was a list of differentially expressed genes of varying significance. The breast cancer metastasis gene signature was defined as the top 500 genes by p-value from this list.

Identification of Candidate Inhibitors of Metastasis

Without wishing to being bound to any particular theory, one method of inhibiting the ability of a tumor to metastasize is to identify drugs that reverse the breast cancer metastasis gene signature. In other words, drugs which best reverse pathologic gene expression signatures of primary tumors in patients with evident local invasion or frank metastasis better reflect primary tumors of patients with localized disease. Mechanisms by which tumors can spread to other tissues were sought rather than drugs that would kill cancer cells.

Cosiner™ used data from the NIH Library of Integrated Network-based Cellular Structures (LINCS) and the BROAD Institute Connectivity Map (CMap) databases, which are comprised of gene expression data for a diverse panel of tumor cell lines treated by a large number of compounds at several exposure time points and drug doses. The LINCS and CMap databases are incorporated herein by reference in their entirety Cosiner™ compared a given signature against the libraries of gene expression responses of cell lines to various compounds and ranked the resulting reversal according to a score, called a similarity score (e.g., based on the mathematical property, e.g., the cosine similarity). The more negative the value of the similarity score, the more complete reversal of the input signature. The algorithm agglomerates results across all available cell lines and outputs a ranked list of compounds according to their potential to reverse the signature. As described in the methods and materials section of this example, this list was further filtered to find the most prominent signals across multiple doses. The filtered and ranked Cosiner™ results for the breast cancer metastasis signature revealed multiple GSK3 inhibitors amongst the top hits and are listed in Table 6.

TABLE 6

Top 10 most robust predictions from Cosiner™ regarding drug reversal of the metastatic breast cancer signature.

| Compound | Top Target | Database (peak reversal) | Time (hrs) | Dose [μM] (peak reversal) | Peak Reversal (similarity score) | # Subsequent significant points |
|---|---|---|---|---|---|---|
| CHIR-99021 | GSK3A | lincs_phase2 | 24 | 10 | −0.0414 | 3 |
| Compound2 | | lincs_phase1 | 6 | 10 | −0.0387 | 4 |
| 6-BIO* | GSK3A* | lincs_phase2 | 24 | 0.4 | −0.0378 | 4 |
| Compound4 | | lincs_phase2 | 24 | 0.04 | −0.0348 | 4 |
| Compound5 | | lincs_phase1 | 6 | 10 | −0.0340 | 6 |
| 6-BIO | GSK3A | lincs_phase1 | 6 | 0.4 | −0.0318 | 3 |
| Compound7 | | lincs_phase1 | 24 | 0.08 | −0.0316 | 3 |
| Compound8 | | lincs_phase2 | 24 | 0.1 | −0.0314 | 4 |
| LY-2090314 | GSK3B | lincs_phase2 | 24 | 0.1 | −0.0304 | 6 |
| Compound10 | | lincs_phase2 | 24 | 3 | −0.0268 | 3 |

*The first instance of 6-BIO was labeled in the output as chembl2178734, which was later identified as 6-BIO.

Figure 7A:
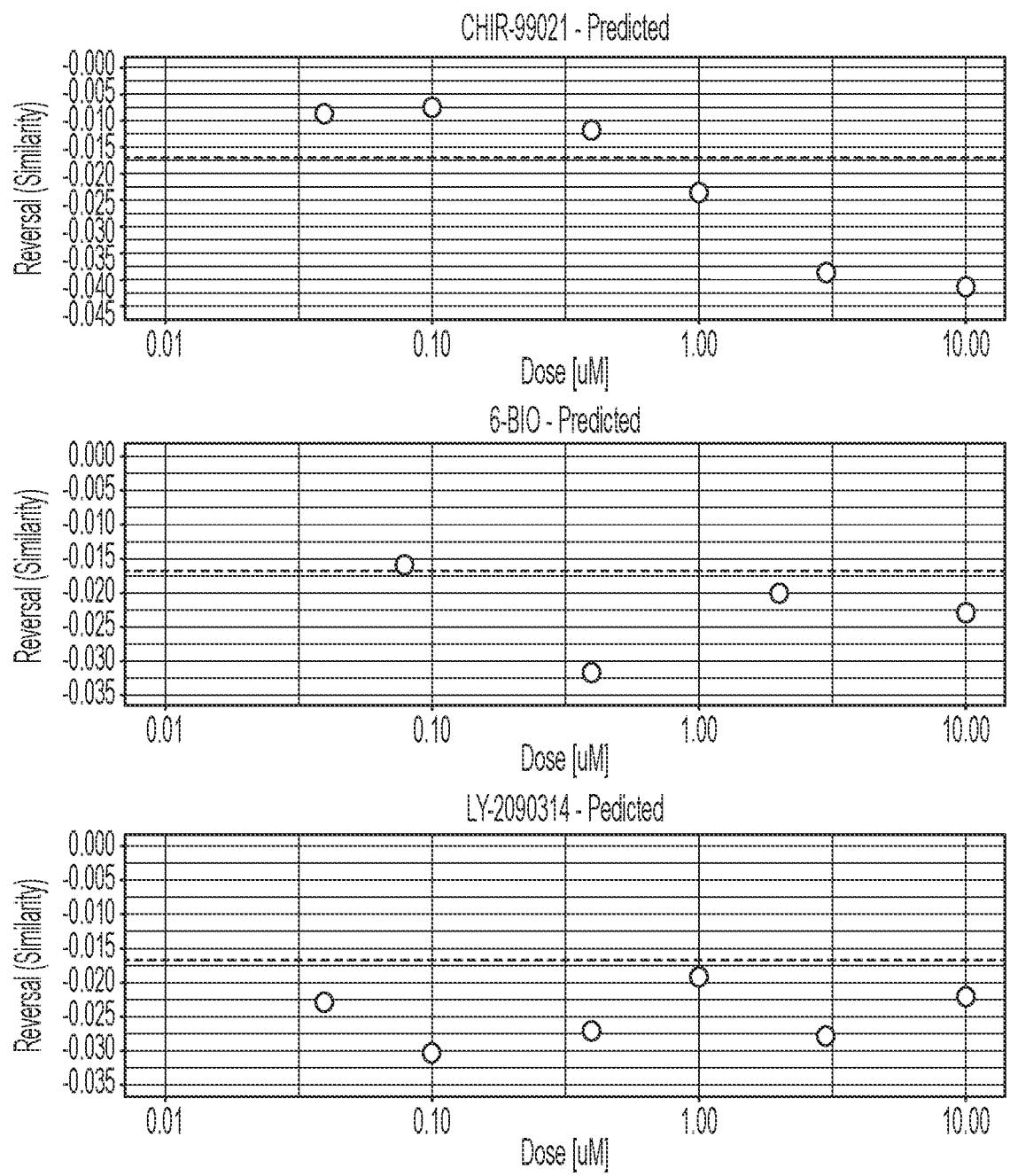
FIG. 7A is a graph of the similarity values of the MDA-MB-231 cell line generated via Cosiner™ for three GSK3 inhibitors using the dataset/time point listed in Table 1. The dotted line is indicative of atop 5% observed similarity score (−0.0168), which is what was used as a "significant similarity score" indicative of significant reversal.

A predicted dose response for each of the top GSK3A/GSK3B inhibitors by plotting similarity score versus dose is shown in FIG. 7A. CHIR-99021 was predicted to have a dose response with a transition concentration around 1 µM. At concentrations higher than 1 µM, Cosiner™ predicted CHIR-99021 to effectively reverse the metastatic signature and thus inhibit metastasis. Additionally, LY-2090314 and 6-BIO's predicted dose responses appeared to be more graded. Most of the points within the treatment groupings were found to be significant. As a result, more of a flat dose response was anticipated, where the drugs are effective at inhibiting metastasis at concentrations greater than 0.04 µM for LY-2090314 and 0.4 µM for 6-BIO.

Figure 7B:
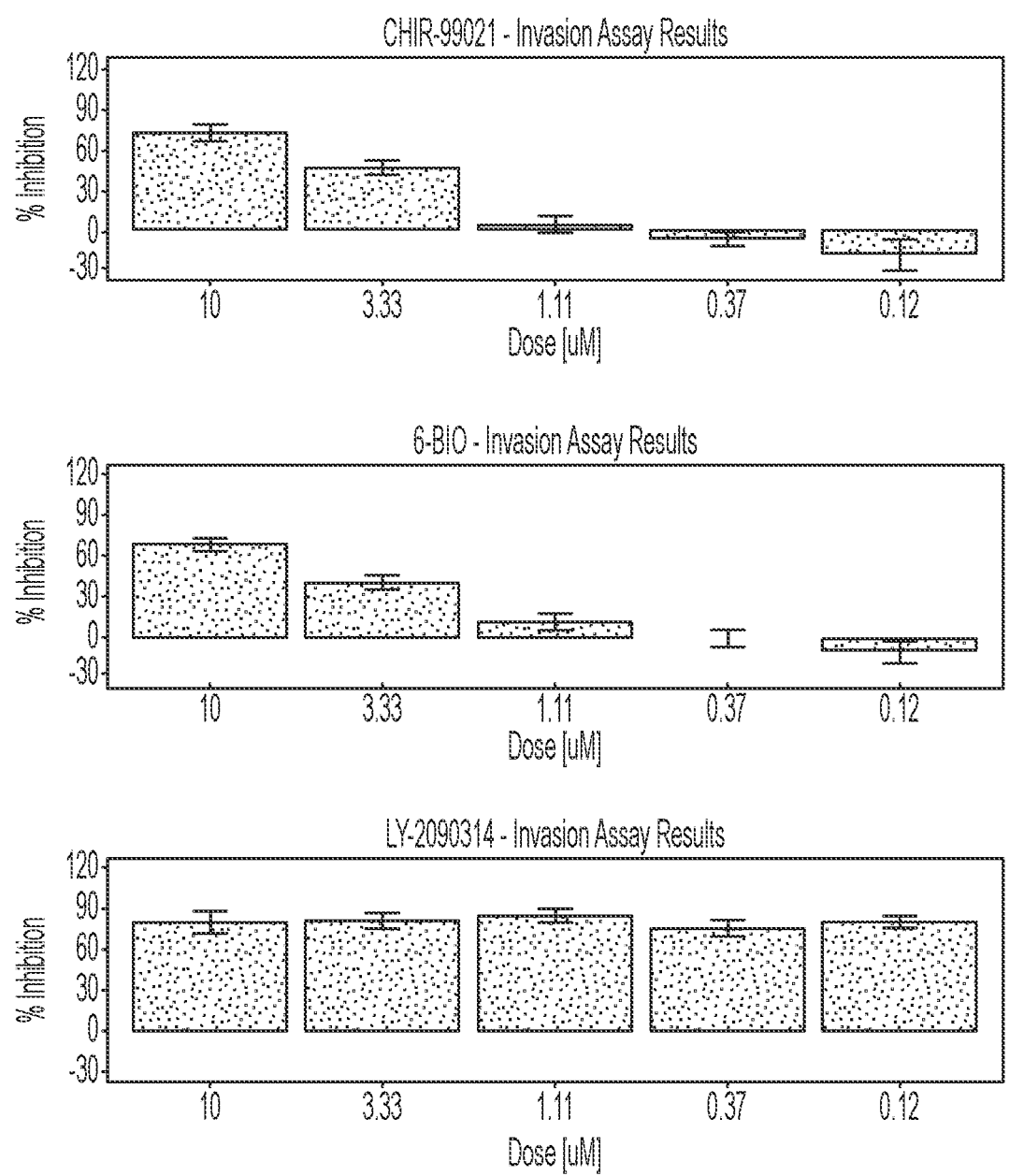
FIG. 7B is a graph of the experimental results of three GSK3 inhibitors in an invasion assay of MDA-MB-231 cells. The error bars represent ±1 standard deviation.

To experimentally test the in silico predictions made by Cosiner™ and to pursue an inhibitor of metastasis, an in vitro ECM-based invasion assay was performed. An invasion assay is an in vitro proxy for the process of cells migrating and breaking through the extracellular matrix as would occur in the body during metastasis. All three GSK3A/GSK3B inhibitors tested were effective at inhibiting the invasion of the human triple negative breast cancer cell model MDA-MB-231 cells (FIG. 7B). The predictions for the dose responses accurately mirrored both CHIR-99021 and LY-2090314 drug dose responses. All three inhibitors are candidates for further development, and without being bound to any particular theory more generally the data suggest that GSK3A/GSK3B represent viable targets to curtail cancer metastasis. LY-2090314 inhibited tumor cell invasion at all concentrations tested and had no significant effect on cell viability, which was approximately equal to 100%. Cell viability was determined at 10 µM by CellTiter-Glo® (CTG). 6-BIO and CHIR-99021 inhibited tumor cell invasion but only at the higher dose levels tested (e.g., 1-10 µM). At 10 µM doses, off-target effects can confound pharmacologic interpretations not to mention that it is unlikely to be a physiologically feasible dose for mice or humans. The viability at for each of the line as tested with each of these drugs was 76.4% for CHIR-99021 and 80.5% for 6-BIO 10 µM of drug by CTG. Therefore, all subsequent biologic testing focused on LY-2090314, as a model GSK3 inhibitor.

Further Characterization of LY-2090314 as an Inhibitor of Metastasis

Figure 8:
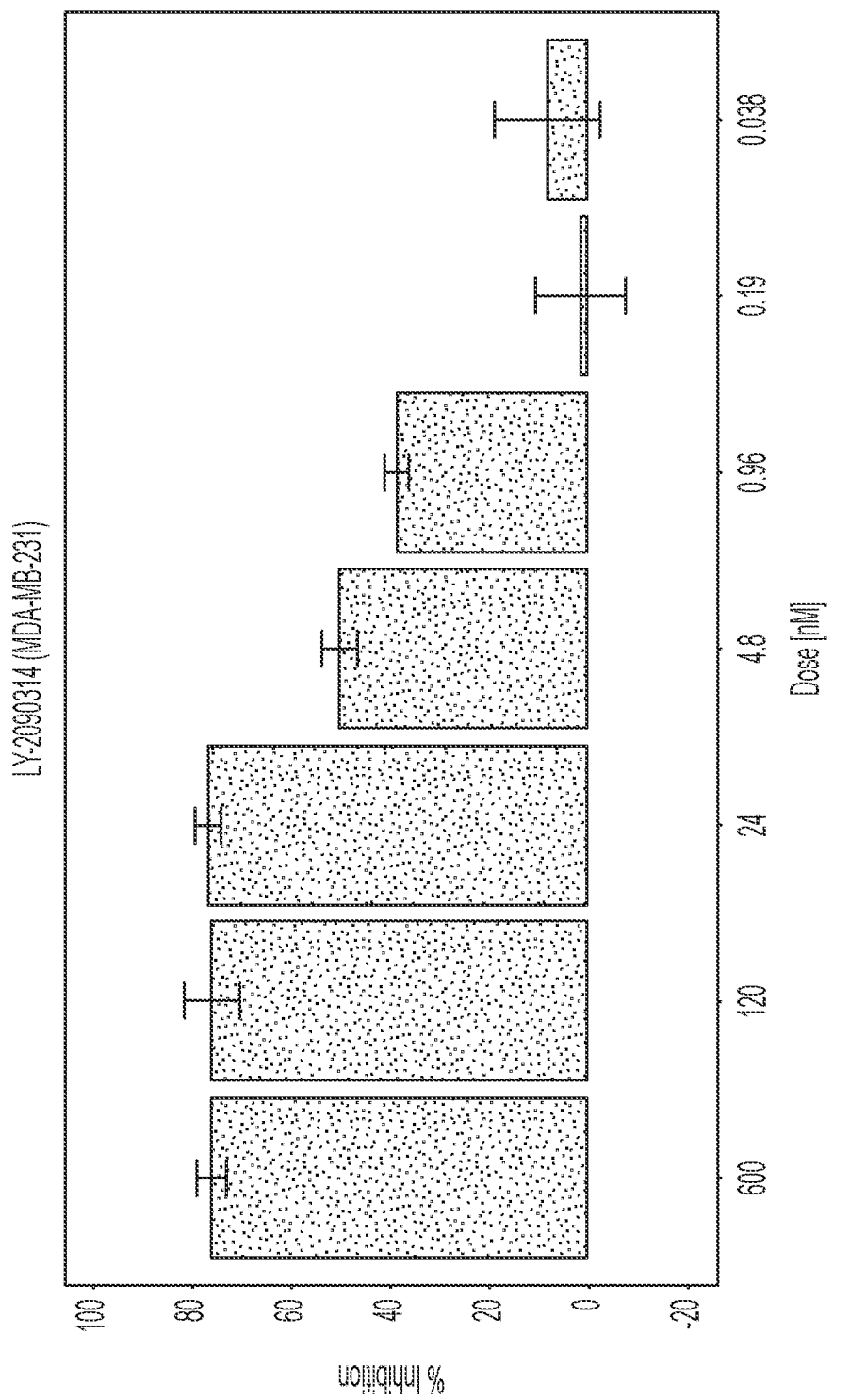
FIG. 8 is a graph of LY-2090314 dose response in an invasion assay using MDA-MB-231 tumor cells. The error bars represent ±1 standard deviation.

After the positive initial study of the inhibition of MDA-MB-231 invasion by GSK3 inhibitors, drug potency was further characterized by exploring a larger concentration range of LY-2090314 (FIG. 8). LY-2090314 maximally inhibited tumor cell invasion at doses of approximately 24 nM and achieved 50% inhibition of baseline invasion at approximately 5 nM. Results are an average of 6 wells. Cell viability at 600 nM of drug was determined to be 93.5% by CellTiter-Glo® (CTG). LY-2090314 affects multiple on- and off-target proteins as reported in the CHEMBL database. The half maximal inhibitory concentration (IC50) values of 1.1 nM and 1.5 nM respectively for GSK3B and GSK3A have been reported. The IC50 values for GSK3A and GSK3B correspond well to the IC50 invasion values observed in the invasion assay. The lowest reported inhibitor constant (KI) value for off-target activity is CDK2 at 251.19 nM. Therefore, LY-2090314 invasion inhibition reaches saturation at an order of magnitude lower than the concentration where the first reported off-target effect occurs. Without being bound to any particular theory, these combined results suggest that inhibition of GSK3B and/or GSK3A is the direct target of the observed anti-metastatic effect.

Figure 9A:
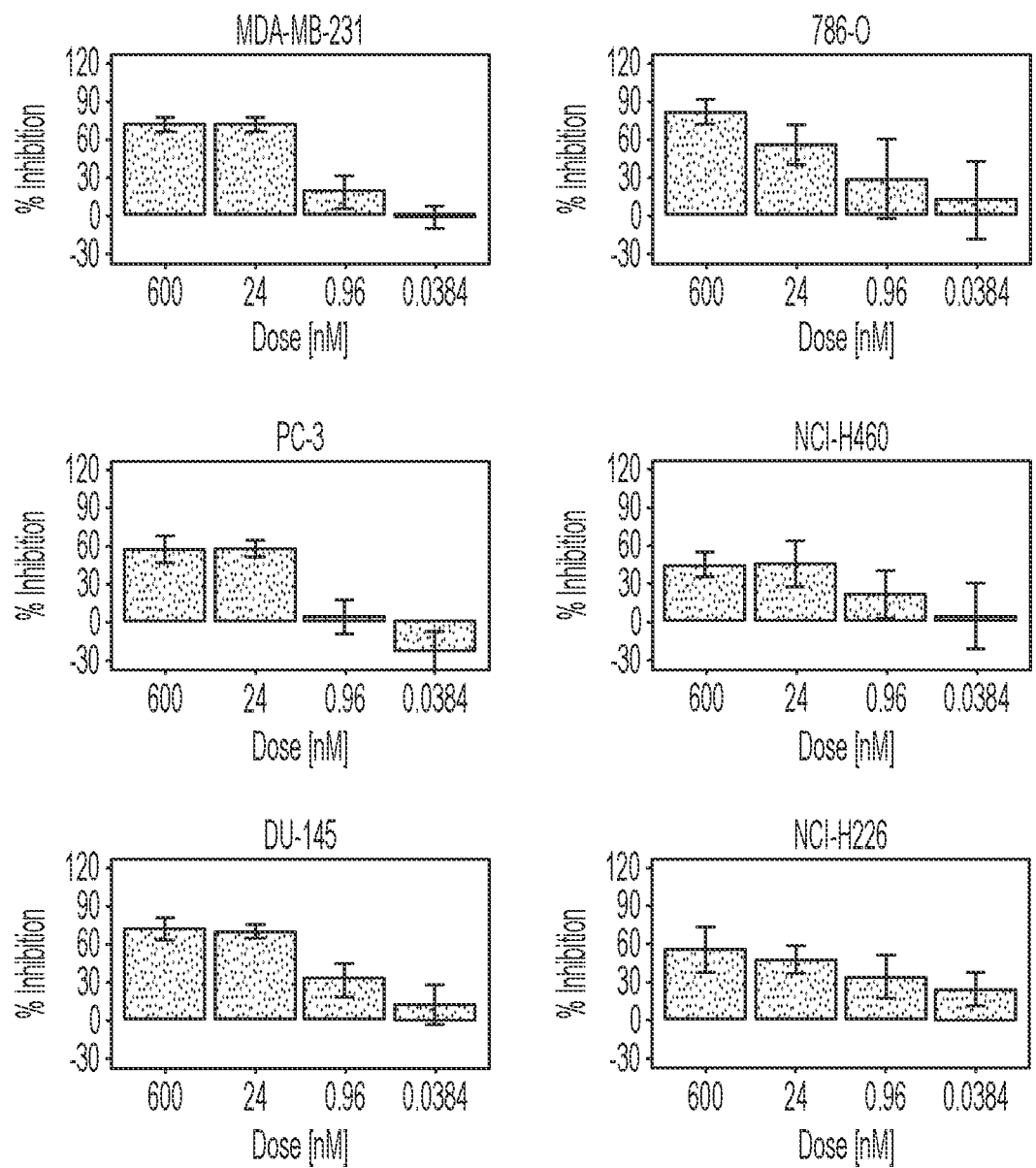
FIG. 9A is a graph of tumor models which were reversed their invasive phenotype when exposed to LY-2090314. The error bars represent ±1 standard deviation.
Figure 9B:
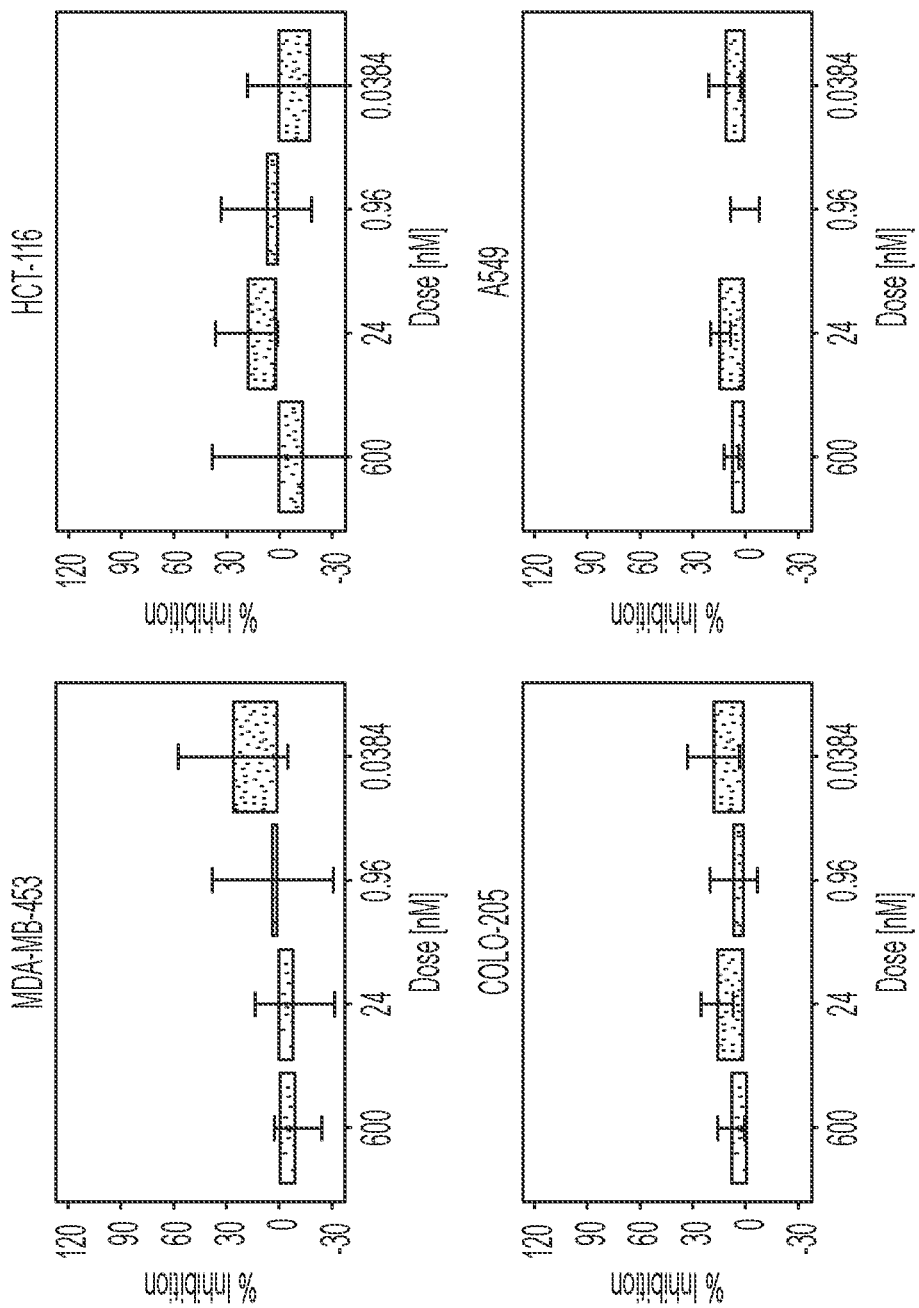
FIG. 9B is a graph of tumor models which were insensitive to LY-2090314 inhibition of invasion. The error bars represent ±1 standard deviation.

LY-2090314 was further characterized by studying its effect on the invasion of a panel of 10 cell lines (FIGS. 9A and 9B). The results for 9 of these 10 cell lines were collected in the same experiment, while the results for A549 came in a previous experiment. Results are an average of 6 wells. LY-2090314 markedly inhibited the invasion of MDA-MB-231 (breast cancer). PC-3 (prostate cancer), DU-145 (prostate cancer), 786-O (renal cancer), NCI-H226 (lung cancer), and NCI-H460 (lung cancer) cells, while not impacting cell viability (FIG. 9A). Cell viability was determined at 600 nM of LY-2090314 for each cell line by CellTiter-Glo® (CTG). The viability for each cell line was as follows: MDA-MB-231=95.5%, PC3≅100%, 786-O=83%, NCI-H460≅100%, DU-145≅100%, and NCI-H226≅100%. It should be noted that LY-2090314-treated 786-O cells had a viability of 83%, which is near the assay's threshold of 80%. LY-2090314 did not significantly inhibit the invasion of MDA-MB-453 (breast cancer), HCT-116 (colon cancer), COLO-205 (colon cancer) and A549 (lung cancer) cells (FIG. 9B). The viability of each cell line was; MDA-MB-453≅100%, HCT-166≅97.7%, COLO-205≅100%, and A549=99.3%. It should be noted that MDA-MB-453 and HCT-116 cells also had low observed baseline invasiveness in the experiments, which can impact assay sensitivity by having a low dynamic range.

Discussion of Example 3

The present example demonstrates the ability of Cosiner™ to identify and recommend GSK3 inhibitors for experimental follow up in the treatment of metastatic breast cancer. The potential of GSK3 inhibitors and, in particular, LY-2090314, as a model drug for GSK3 inhibition, to be used therapeutically as an inhibitor of tumor cell invasion and cancer metastasis was identified in this study through the use of Cosiner™ and its ranking analysis. The analysis lead to other cell types being tested for metastasis inhibition with GSK3. GSK3 inhibition showed a pronounced ability to inhibit invasion in 6/10 (60%) cell lines tested at concentrations at or below 24 nM without having a pronounced impact on tumor cell viability.

Effective scaling combined with low false positive and negative rates enables Cosiner to query the large LINCS gene expression database to identify new candidate therapies for HER2+ breast cancer and to better understand their mode of action. The Library of Integrated Cell Signatures (LINCS)[2] project builds upon the original Connectivity Map (CMAP)[3] project and dramatically increases the number of drugs and cell line conditions profiled. Identification of drugs through gene expression reversal has been shown promising in numerous studies[1,4-7]. By computing a per-gene enrichment statistic, Cosiner further aids drug discovery by providing candidate genes which can act as potential biomarkers and can guide experimental validation. In addition, these per-gene statistics can serve as weights for an additional round of enrichment to identify pathways mediating a therapeutic response. For these reasons, we believe that Cosiner is ideally suited to analyze large pharmacogenomic datasets to systematically generate novel actionable drug hypotheses.

Materials & Methods for Example 3
Materials:

TABLE 7

Reagents utilized in transwell invasion assay

| Reagent | Vendor | Cat# |
|---|---|---|
| 1640 medium | Gibco | 11875-093 |
| Leibovitz's L-15 medium | Gibco | 11415-064 |
| MEM medium | Invitrogen | 11360-070 |
| F12k medium | Hyclone | SH30526.01 |
| DMEM medium | Gibco | 11995-073 |
| Fetal Bovine Serum (FBS) | Gibco | 16000-044 |
| Penicillin-Streptomycin Mixture (100X) | Gibco | 15140-122 |
| DiIC12(3) Fluorescent Dye | BD | 354218 |
| Matrigel ® Matrix | BD | 356234 |
| LY-2090314 | Selleckchem | S7063 |
| CHIR-99021 | Selleckchem | S2924 |
| BIO (aka 6-BIO) | Selleckchem | S7198 |

TABLE 8

Plate materials used in transwell invasion assay

| Consumables | Vendor | Cat# |
|---|---|---|
| BD FalconTM FluoroBlackTM 96-Multiwell Insert system (3 µm pores) | BD | 351162 |
| BD FalconTM FluoroBlackTM 96-Multiwell Insert system (8 µm pores) | BD | 351164 |
| Ultra-low attachment multiwell plates | Corning | 3474 |

TABLE 9

Cell lines used in transwell invasion assay

| Cell Line | Cancer Type | Culture Medium |
|---|---|---|
| 786-O | Renal carcinoma | 1640 + 10% FBS |
| NCI-H460 | Lung carcinoma | 1640 + 10% FBS |
| NCI-H226 | Lung carcinoma | 1640 + 10% FBS |
| MDA-MB-231 | Breast adenocarcinoma | L-15 + 10% FBS |
| DU-145 | Prostate carcinoma | MEM + 10% FBS |
| HCT-116 | Colorectal carcinoma | DMEM + 10% FBS |
| PC-3 | Prostate adenocarcinoma | F12k + 10% FBS |
| MDA-MB-453 | Breast carcinoma | DMEM + 10% FBS |
| COLO-205 | Colorectal adenocarcinoma | 1640 + 10% FBS |
| A549 | Lung cancer | F12K + 10% FBS |

Methods for Example 3:
Transwell Invasion Assay
Cell Starvation:

Culture medium was removed when cells reached 80% confluence. Cultures were gently rinsed with PBS to remove all the remaining serum. Serum-free medium was added to the cultures and they were incubated overnight at 37° C. 5% CO2.

Preparation of Transwell Membranes:

786-O. NCI-H460, NCI-H226, MDA-MB-231 and DU-145 cells were tested in transwells with 3 µm pores. HCT-116, PC-3, MDA-MB-453 and COLO-205 cells were tested in transwells with 8 µm pores.

First, the Matrigel® was thawed in an ice bath in a refrigerator (4° C.) overnight. Matrigel® was then diluted into serum-free, cold cell culture media (1:8 dilution). 20 µL of diluted Matrigel®) was added into each well of BD Falcon™ Multiwell 96-well cell culture inserts. Transwell inserts were incubated at 37° C., for at least 4 to 5 hours for gelling. Before use, the transwells were rehydrated by adding 100 µL PBS to the insert and incubated at 37° C., in ambient air for 2 hours.

Preparation of Cells:

Cells were harvested using Trypsin and washed once with serum free medium. Cells were resuspended with serum-free medium. The 786-O cell density was adjusted to $2\times10^5$ cells/mL; the NCI-H460 and NCI-H226 cell density was adjusted to $5\times10^6$ cells/mL; the MDA-MB-231 and DU-145 cell density was adjusted to $1\times10^6$ cells/mL; the HCT-116 cell density was adjusted to $5\times10^6$ cells/mL; the PC-3 cell density to $1\times10^6$ cell/mL; the MDA-MB-453 cell density was adjusted to $5\times10^5$ cells/mL; and the COLO-205 cell density was adjusted to $2\times10^6$ cells/mL.

Cell Invasion:

Cells were pre-treated with compounds, which were dissolved in DMSO and diluted to the desired concentration in culture medium. The pretreatment was performed in Ultra-low attachment multiwell plates. 90 µL cells and 10 µL compound solution were mixed in each well of the plate. The plate was covered with a lid and incubated for 60 minutes. 50 µL of cells was seeded onto each top insert, which was pre-coated with 1:8 diluted Matrigel®. 180 µL of warm (37° C.) culture medium containing 10% FBS was added to the lower chamber of the transwell plate. 200 µL serum-free medium and 20 µL of compound dilution was added to the indicated lower chamber as the negative control. The 96-Multiwell Insert system was transferred to the incubator for 16 hours at 37° C., and 5% $CO_2$. Next, the insert was transferred to a new plate. The lower chambers were centrifuged at 3000 rpm for 5 minutes and then washed twice with PBS.

Measurement of Invasive Signal:

The insert was transferred back to the lower chamber and 200 µL of the DiTC12(3) fluorescent dye solution was added. The final concentration of DiIC12(3) was 5 µg/mL. Plates were incubated for 30 minutes at 37° C., and 5% $CO_2$. The plates were then washed with PBS twice. The invaded/migrated cells were monitored by reading fluorescence at 530/590 nm on a PerkinElmer EnSpire™ plate reader.

Percent inhibition for compound was calculated using Formula 6.

$$\% \text{Inhibition} = 100\% \times \frac{\text{Positive} - \text{Compound}}{\text{Positive} - \text{Negative}} \qquad \text{Formula 6}$$

The positive control was DMSO treated and had medium with 10% FBS (average of 3 wells per cell line) in receiver well. The negative control was DMSO treated with no FBS in the receiver well (average of 3 wells per cell line). Samples pre-treated with compound had 10% FBS attractant (6 wells per condition) in the receiver well.

Viability Measurement:

Viability was determined at the maximum drug concentration measured in a given experiment via CellTiter-Glo® (CTG) per manufacturers recommendations: https://www.promega.com/-/media/files/resources/protocols/technical-bulletins/0/celltiter-glo-luminescent-cell-viability-assay-protocol.pdf?la=en.

Computational Data Acquisition

The TCGA (http://cancergenome.nih gov/) breast invasive carcinoma dataset (BRCA) was selected for analysis and its RNA-seq data in the form of raw counts were downloaded from the Firehose web portal along with the clinical metadata. TCGA is incorporated herein by reference in its entirety Identification of Metastasis-Associated Genes The comparison used to find primary tumor markers of metastasis was patients with lymph node involvement (defined as the N123 group—patients with any pathologic_n values including N1, N2, and N3) vs. patients with no lymph node involvement, including no distant metastases (defined as N0_not_M1 group—patients with pathologic_n value of N0 and all pathologic_m values not including those with M1). In total, before processing and QC, there were 558 N123 patients and 332 N0_not_M1 patients.

Lowly expressed genes were excluded prior to performing differential gene expression analysis. To enter the analysis, a given gene needed to have more than 10 CPM (counts per million) in at least a fraction of the samples defined by the smallest group (in this case 332 patients—N0_not_M1). Voom was used to compute observation-level weights that account for the mean-variance relationship observed in RNA-seq data. Voom-transformed expression data along with Plate ID (categorical covariate) were inputted into limma to identify differentially expressed genes between N123 and N0_not_M1 patients while adjusting for potential batch effects. Limma was used to implement the limma-voom differential expression analysis. Some plates were excluded due to having only 1 or 2 samples per plate, which would not be enough to account for batch effects (Plate_A10U, Plate_A26B, Plate_A32Y, and Plate_A466). This resulted in 885 total samples entering the BRCA analysis (554 N123 and 331 N0_not_M1). The top 500 genes by nominal p-value were considered to be the breast cancer metastasis signature in subsequent analyses.

Systematic Identification of Anti-Metastasis Drug Candidates

A drug signature database was assembled by combining data generated as part of the LINCS and CMAP projects. These two databases are incorporated herein by reference in their entirety. For each concentration, time point and database combination, signatures were generated using limma. The breast cancer metastasis-associated 500 gene signature was queried against the drug signature database using cosine similarity of the moderated t-statistic to assess gene expression reversal to identify novel drug candidates that can reverse metastasis.

To further refine the list of potential drug candidates, a filtering system was implemented within Cosiner™. First, a threshold similarity value was defined to contain the top 5% of reversal similarity scores. In the case of breast cancer, this value was −0.0168. Any value lower was indicative of significant reversal of the breast cancer signature. To make the final list of robust potential drug candidates, a candidate needed to have at least 3 subsequent doses with similarity values more negative than the threshold value in at least 1 dataset and time point (e.g. LINCS Phase 2, 24 hours). The candidate also needed to have either a majority of its data points more negative than the threshold in at least 1 dataset/time point or a negative slope across its data points in the dataset/time point that had at least 3 significant subsequent doses. The slope was determined in MATLAB via the linear regression "/" operator and was declared "negative" if it was below −0.001. This resulted in the most robust set of predictions which had a predicted dose response and was supported by multiple data points.

REFERENCES

1. Lamb, J. et al. The Connectivity Map: Using Gene-Expression Signatures to Connect Small Molecules, Genes, and Disease. Science 313, 1929-1935 (2006).
2. Keenan, A. B. et al. The Library of Integrated Network-Based Cellular Signatures NIH Program: System-Level Cataloging of Human Cells Response to Perturbations. Cell Syst. (2017). doi:10.1016/j.cels.2017.11.001
3. Lamb, J. et al. The Connectivity Map: Using Gene-Expression Signatures to Connect Small Molecules, Genes, and Disease. Science 313, 1929-1935 (2006).
4. Lucas, F. A. S. et al. Cancer In Silico Drug Discovery: A Systems Biology Tool for Identifying Candidate Drugs to Target Specific Molecular Tumor Subtypes. *Mol. Cancer Ther.* 13, 3230-3240 (2014).
5. Fowler, K. D. et al. Leveraging existing data sets to generate new insights into Alzheimer's disease biology in specific patient subsets. *Sci. Rep.* 5, 14324 (2015).
6. Lee, H., Kang, S. & Kim, W. Drug Repositioning for Cancer Therapy Based on Large-Scale Drug-Induced Transcriptional Signatures. *PLOS ONE* 11, e0150460 (2016).
7. Ferguson, L. B. et al. Genome-Wide Expression Profiles Drive Discovery of Novel Compounds that Reduce Binge Drinking in Mice. *Neuropsychopharmacology* (2017). doi:10.1038/npp.2017.301

Computer System and Network Environment

Figure 10:
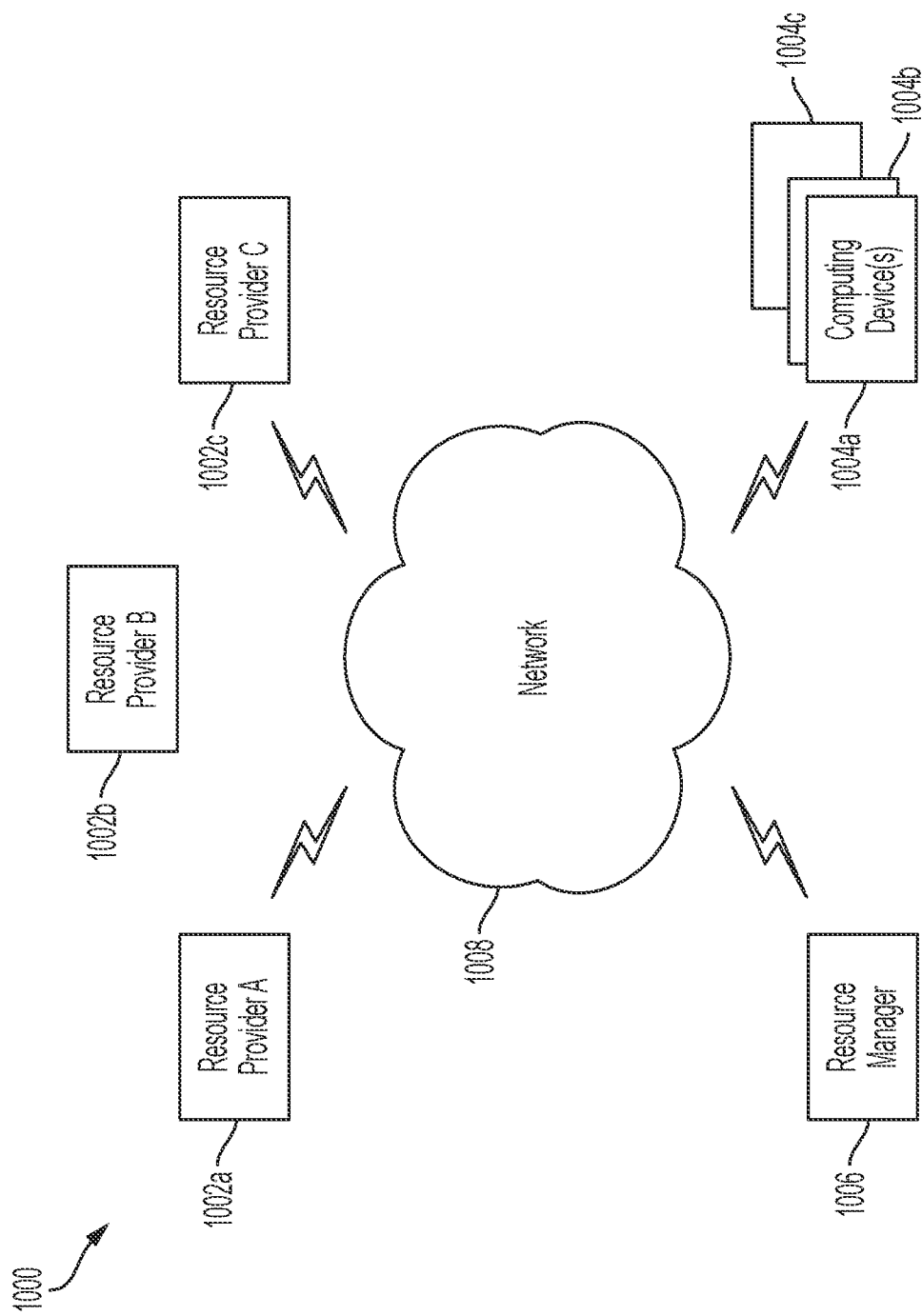
FIG. 10 is a block diagram of an exemplary cloud computing environment, used in certain embodiments.

As shown in FIG. 10, an implementation of a network environment 100 for use in providing systems, methods, and architectures as described herein is shown and described. In brief overview, referring now to FIG. 10, a block diagram of an exemplary cloud computing environment 1000 is shown and described. The cloud computing environment 1000 may include one or more resource providers 1002a, 1002b, 1002c (collectively, 1002). Each resource provider 1002 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 1002 may be connected to any other resource provider 1002 in the cloud computing environment 1000. In some implementations, the resource providers 1002 may be connected over a computer network 1008. Each resource provider 1002 may be connected to one or more computing device 1004a, 1004b, 1004c (collectively, 1004), over the computer network 1008.

The cloud computing environment 1000 may include a resource manager 1006. The resource manager 1006 may be connected to the resource providers 1002 and the computing devices 1004 over the computer network 1008. In some implementations, the resource manager 1006 may facilitate the provision of computing resources by one or more resource providers 1002 to one or more computing devices 1004. The resource manager 1006 may receive a request for a computing resource from a particular computing device 1004. The resource manager 1006 may identify one or more resource providers 1002 capable of providing the computing resource requested by the computing device 1004. The resource manager 1006 may select a resource provider 1002 to provide the computing resource. The resource manager 1006 may facilitate a connection between the resource provider 1002 and a particular computing device 1004. In some implementations, the resource manager 1006 may establish a connection between a particular resource provider 1002 and a particular computing device 1004. In some implementations, the resource manager 1006 may redirect a particular computing device 1004 to a particular resource provider 1002 with the requested computing resource.

Figure 11:
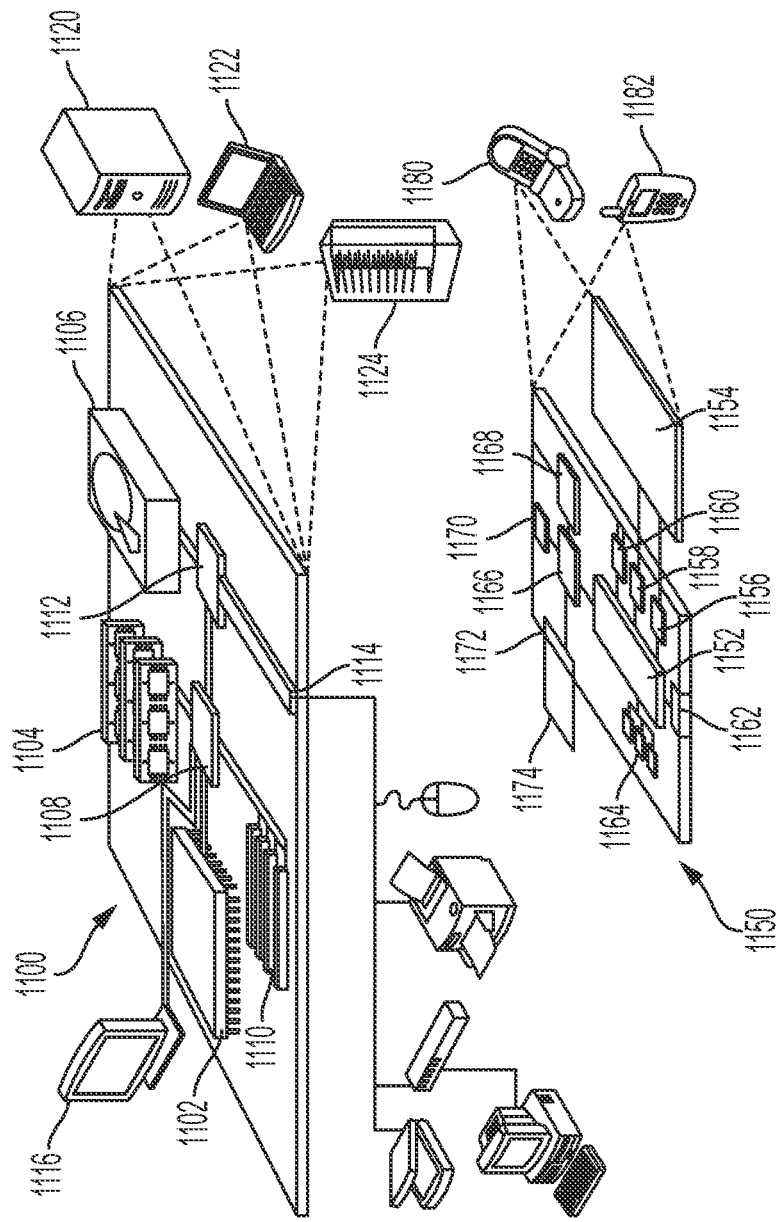
FIG. 11 is a block diagram of an example computing device and an example mobile computing device used in certain embodiments.

FIG. 11 shows an example of a computing device 1100 and a mobile computing device 1150 that can be used to implement the techniques described in this disclosure. The computing device 1100 is intended to represent various forms of digital computers, such as laptops, desktops, workstations, personal digital assistants, servers, blade servers, mainframes, and other appropriate computers. The mobile computing device 1150 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 1100 includes a processor 1102, a memory 1104, a storage device 1106, a high-speed interface 1108 connecting to the memory 1104 and multiple high-speed expansion ports 1110, and a low-speed interface 1112 connecting to a low-speed expansion port 1114 and the storage device 1106. Each of the processor 1102, the memory 1104, the storage device 1106, the high-speed interface 1108, the high-speed expansion ports 1110, and the low-speed interface 1112, are interconnected using various busses, and may be mounted on a common motherboard or in other manners as appropriate. The processor 1102 can process instructions for execution within the computing device 1100, including instructions stored in the memory 1104 or on the storage device 1106 to display graphical information for a GUI on an external input/output device, such as a display 1116 coupled to the high-speed interface 1108. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system). Thus, as the term is used herein, where a plurality of functions are described as being performed by "a processor", this encompasses embodiments wherein the plurality of functions are performed by any number of processors (one or more) of any number of computing devices (one or more). Furthermore, where a function is described as being performed by "a processor", this encompasses embodiments wherein the function is performed by any number of processors (one or more) of any number of computing devices (one or more) (e.g., in a distributed computing system).

The memory 1104 stores information within the computing device 1100. In some implementations, the memory 1104 is a volatile memory unit or units. In some implementations, the memory 1104 is a non-volatile memory unit or units. The memory 1104 may also be another form of computer-readable medium, such as a magnetic or optical disk.

The storage device 1106 is capable of providing mass storage for the computing device 1100. In some implementations, the storage device 1106 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 1102), perform one or more methods, such as those described above. The instructions can also be stored by one or more storage devices such as computer- or machine-readable mediums (for example, the memory 1104, the storage device 1106, or memory on the processor 1102).

The high-speed interface 1108 manages bandwidth-intensive operations for the computing device 1100, while the low-speed interface 1112 manages lower bandwidth-intensive operations. Such allocation of functions is an example only. In some implementations, the high-speed interface 1108 is coupled to the memory 1104, the display 1116 (e.g., through a graphics processor or accelerator), and to the high-speed expansion ports 1110, which may accept various expansion cards (not shown). In the implementation, the low-speed interface 1112 is coupled to the storage device 1106 and the low-speed expansion port 1114. The low-speed expansion port 1114, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 1100 may be implemented in a number of different forms, as shown in the figure. For example, it may be implemented as a standard server 1120, or multiple times in a group of such servers. In addition, it may be implemented in a personal computer such as a laptop computer 1122. It may also be implemented as part of a rack server system 1124. Alternatively, components from the computing device 1100 may be combined with other components in a mobile device (not shown), such as a mobile computing device 1150. Each of such devices may contain one or more of the computing device 1100 and the mobile computing device 1150, and an entire system may be made up of multiple computing devices communicating with each other.

The mobile computing device 1150 includes a processor 1152, a memory 1164, an input/output device such as a display 1154, a communication interface 1166, and a transceiver 1168, among other components. The mobile computing device 1150 may also be provided with a storage device, such as a micro-drive or other device, to provide additional storage. Each of the processor 1152, the memory 1164, the display 1154, the communication interface 1166, and the transceiver 1168, are interconnected using various buses, and several of the components may be mounted on a common motherboard or in other manners as appropriate.

The processor 1152 can execute instructions within the mobile computing device 1150, including instructions stored in the memory 1164. The processor 1152 may be implemented as a chipset of chips that include separate and multiple analog and digital processors. The processor 1152 may provide, for example, for coordination of the other components of the mobile computing device 1150, such as control of user interfaces, applications run by the mobile computing device 1150, and wireless communication by the mobile computing device 1150.

The processor 1152 may communicate with a user through a control interface 1158 and a display interface 1156 coupled to the display 1154. The display 1154 may be, for example, a TFT (Thin-Film-Transistor Liquid Crystal Display) display or an OLED (Organic Light Emitting Diode) display, or other appropriate display technology. The display interface 1156 may comprise appropriate circuitry for driving the display 1154 to present graphical and other information to a user. The control interface 1158 may receive commands from a user and convert them for submission to the processor 1152. In addition, an external interface 1162 may provide communication with the processor 1152, so as to enable near area communication of the mobile computing device 1150 with other devices. The external interface 1162 may provide, for example, for wired communication in some implementations, or for wireless communication in other implementations, and multiple interfaces may also be used.

The memory 1164 stores information within the mobile computing device 1150. The memory 1164 can be implemented as one or more of a computer-readable medium or media, a volatile memory unit or units, or a non-volatile memory unit or units. An expansion memory 1174 may also be provided and connected to the mobile computing device 1150 through an expansion interface 1172, which may include, for example, a SIMM (Single In Line Memory Module) card interface. The expansion memory 1174 may provide extra storage space for the mobile computing device 1150, or may also store applications or other information for the mobile computing device 1150. Specifically, the expansion memory 1174 may include instructions to carry out or supplement the processes described above, and may include secure information also. Thus, for example, the expansion memory 1174 may be provide as a security module for the mobile computing device 1150, and may be programmed with instructions that permit secure use of the mobile computing device 1150. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier, that the instructions, when executed by one or more processing devices (for example, processor 1152), perform one or more methods, such as those described above. The instructions can also be stored by one or more storage devices, such as one or more computer- or machine-readable mediums (for example, the memory 1164, the expansion memory 1174, or memory on the processor 1152). In some implementations, the instructions can be received in a propagated signal, for example, over the transceiver 1168 or the external interface 1162.

The mobile computing device 1150 may communicate wirelessly through the communication interface 1166, which may include digital signal processing circuitry where necessary. The communication interface 1166 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 1168 using a radio-frequency. In addition, short-range communication may occur, such as using a Bluetooth®, Wi-Fi™, or other such transceiver (not shown). In addition, a GPS (Global Positioning System) receiver module 1170 may provide additional navigation- and location-related wireless data to the mobile computing device 1150, which may be used as appropriate by applications running on the mobile computing device 1150.

The mobile computing device 1150 may also communicate audibly using an audio codec 1160, which may receive spoken information from a user and convert it to usable digital information. The audio codec 1160 may likewise generate audible sound for a user, such as through a speaker, e.g., in a handset of the mobile computing device 1150. Such sound may include sound from voice telephone calls, may include recorded sound (e.g., voice messages, music files, etc.) and may also include sound generated by applications operating on the mobile computing device 1150.

The mobile computing device 1150 may be implemented in a number of different forms, as shown in the figure. For example, it may be implemented as a cellular telephone 1180. It may also be implemented as part of a smart-phone 1182, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback): and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In some implementations, modules described herein can be separated, combined or incorporated into single or combined modules. The modules depicted in the figures are not intended to limit the systems described herein to the software architectures shown therein.

Elements of different implementations described herein may be combined to form other implementations not specifically set forth above. Elements may be left out of the processes, computer programs, databases, etc, described herein without adversely affecting their operation. In addition, the logic flows depicted in the figures do not require the particular order shown, or sequential order, to achieve desirable results. Various separate elements may be combined into one or more individual elements to perform the functions described herein.

Throughout the description, where apparatus and systems are described as having, including, or comprising specific components, or where processes and methods are described as having, including, or comprising specific steps, it is contemplated that, additionally, there are apparatus, and systems of the present invention that consist essentially of, or consist of, the recited components, and that there are processes and methods according to the present invention that consist essentially of, or consist of, the recited processing steps.

INCORPORATION BY REFERENCE

All publications mentioned herein are hereby incorporated by reference in their entirety as if each individual publication or patent was specifically and individually indicated to be incorporated by reference.

What is claimed is:

1. A system for identifying a candidate therapy for treatment of a disease, the system comprising:
   a processor; and
   a memory having instructions stored thereon, wherein the instructions, when executed by the processor, cause the processor to:
   (a) identify a first gene set comprising differentially expressed genes of cells indicative of the disease as compared to cells not indicative of the disease, wherein the first gene set is represented as a first numeric vector comprising weighted values corresponding to gene expression data of the differentially expressed genes of the first gene set;
   (b) for each of a plurality of candidate therapies causing changes in gene expression of cells:
      (i) identify a second gene set corresponding to each of said candidate therapies, wherein the second gene set is represented as a second numeric vector comprising weighted values corresponding to gene expression data of differentially expressed genes of cells treated with said candidate therapy as compared to cells not treated with said candidate therapy; and
      (ii) determine a measure of similarity between the first gene set and the second gene set using the first numeric vector and the second numeric vector, wherein the measure of similarity is a function of an angle between the first numeric vector and the second numeric vector; and
   (c) identify one or more members of the plurality of candidate therapies as candidates for treatment of the disease using the measures of similarity.

2. The system of claim 1, wherein the disease is metastatic cancer.

3. The system of claim 1, wherein the candidate therapy comprises a drug or a combination of drugs.

4. The system of claim 1, wherein at least one of the plurality of candidate therapies comprises a schedule for administering said candidate therapy.

5. The system of claim 1, wherein the measure of similarity between the first gene set and the second gene set using the first numeric vector and the second numeric vector quantifies a distance between the first numeric vector and the second numeric vector.

6. The system of claim 1, wherein the measure of similarity between the first gene set and the second gene set using the first numeric vector and the second numeric vector quantifies a cosine similarity for the first numeric vector and the second numeric vector.

7. The system of claim 1, wherein the measure of similarity between the first gene set and the second gene set using the first numeric vector and the second numeric vector comprises a use of sparse matrix linear algebra.

8. The system of claim 1, wherein the instructions cause the processor to identify the first gene set comprising differentially expressed genes of metastatic cancer cells as compared to non-metastatic cancer cells.

9. The system of claim 8, wherein the instructions cause the processor to identify the first gene set comprising differentially expressed genes of primary tumor cells from patients with lymph node metastasis as compared to primary tumor cells from patients without lymph node metastasis.

10. The system of claim 8, wherein the instructions cause the processor to identify the first gene set comprising differentially expressed genes of HER2+ (human epidermal growth factor receptor 2 positive) breast cancer cells as compared to HER2− (human epidermal growth factor receptor 2 negative) breast cancer cells.

11. The system of claim 1, wherein at least one of the plurality of candidate therapies is a small molecule.

12. The system of claim 1, wherein at least one of the plurality of candidate therapies is an inhibitory agent.

13. The system of claim 1, wherein the instructions, when executed by the processor, cause the processor to compute per-gene enrichment statistics and use the per-gene enrichment statistics to identify a drug mechanism.

14. The system of claim 13, wherein the instructions, when executed by the processor, cause the processor to use the per-gene enrichment statistics to identify a gene set of interest that is enriched within weighted overlap genes.

15. The system of claim 14, wherein the weighted overlap genes are weighted by their partial cosines.

16. The system of claim 1, wherein at least one of the plurality of candidate therapies comprises a drug or a combination of drugs.

17. The system of claim 1, wherein the measure of similarity is a function of the magnitudes of the first numeric vector and the second numeric vector.

18. The system of claim 17, wherein the measure of similarity is normalized by the magnitudes of the first numeric vector and the second numeric vector.

19. The system of claim 1, wherein step (a) comprises identifying the first gene set corresponding to RNA-seq data of cells indicative of the disease and RNA-seq data of cells not indicative of the disease.

20. The system of claim 1, wherein step (a) comprises identifying the first gene set corresponding to microarray data of cells indicative of the disease and microarray data of cells not indicative of the disease.

21. The system of claim 1, wherein step (b) comprises identifying a second gene set corresponding to each candidate therapy using a library of gene expression signatures.

22. The system of claim 21, wherein the library of gene expression signatures comprises signatures indicative of human cell responses to perturbations.

23. The system of claim 1, wherein step (b) comprises identifying a second gene set corresponding to each candidate therapy using a library comprising microarray data.

24. A method for identifying a candidate therapy for treatment of a disease, the method comprising:
   (a) identifying, by a processor of a computing device, a first gene set comprising differentially expressed genes of cells indicative of the disease as compared to cells not indicative of the disease, wherein the first gene set is represented as a first numeric vector comprising weighted values corresponding to gene expression data of the differentially expressed genes of the first gene set;
   (b) for each of a plurality of candidate therapies causing changes in gene expression of cells:
      (i) identifying, by the processor, a second gene set corresponding to said candidate therapy, wherein the second gene set is represented as a second numeric vector comprising weighted values corresponding to gene expression data of differentially expressed genes of cells treated with said candidate therapy as compared to cells not treated with said candidate therapy; and
      (ii) determining, by the processor, a measure of similarity between the first gene set and the second gene set using the first numeric vector and the second numeric vector, wherein the measure of similarity is a function of an angle between the first numeric vector and the second numeric vector; and
   (c) identifying, by the processor, one or more members of the plurality of candidate therapies as candidates for treatment of the disease using the measures of similarity.

25. The method of claim 24, wherein the candidate therapy comprises a drug or a combination of drugs.

26. The method of claim 24, wherein at least one of the plurality of candidate therapies comprises a schedule for administering said candidate therapy.

27. The method of claim 24, wherein the disease is metastatic cancer.

28. The method of claim 24, wherein the measure of similarity between the first gene set and the second gene set using the first numeric vector and the second numeric vector quantifies a distance between the first numeric vector and the second numeric vector.

29. The method of claim 24, wherein the measure of similarity between the first gene set and the second gene set using the first numeric vector and the second numeric vector quantifies a cosine similarity for the first numeric vector and the second numeric vector.

30. The method of claim 24, wherein the measure of similarity between the first gene set and the second gene set using the first numeric vector and the second numeric vector comprises a use of sparse matrix linear algebra.

31. The method of claim 24, further comprising computing, by the processor, per-gene enrichment statistics and using, by the processor, the per-gene enrichment statistics to identify a drug mechanism.

32. The method of claim 31, wherein the method comprises using the per-gene enrichment statistics that identify the drug mechanism to plan follow-up experiments.

33. The method of claim 31, wherein the method comprises using the per-gene enrichment statistics that identify the drug mechanism to identify key genes driving overall enrichment.

34. The method of claim 31, wherein the method comprises using the per-gene enrichment statistics that identify the drug mechanism to identify a gene set of interest enriched within weighted overlap genes.

35. The method of claim 34, wherein the weighted overlap genes are weighted by their partial cosines.

36. A system for analyzing sets of genes, the system comprising:
   a processor; and
   a memory having instructions stored thereon, wherein the instructions, when executed by the processor, cause the processor to:
      (a) identify a first gene set corresponding to the disease, the first gene set comprising differentially expressed genes of cells indicative of the disease as compared to cells not indicative of the disease, wherein the first gene set is represented as a first numeric vector comprising weighted values corresponding to gene expression data of the differentially expressed genes of the first gene set; and
      (b) for each of a plurality of candidate therapies:
         (i) identify a second gene set corresponding to the candidate therapy, wherein the second gene set is represented as a second numeric vector comprising weighted values corresponding to gene expression data of differentially expressed genes; and
         (ii) compute a per-gene enrichment statistic for each gene of a subset of the first gene set using the first numeric vector and the second numeric vector.

37. The system of claim 36, further comprising using the per-gene enrichment statistics to identify a drug mechanism for treatment of the disease.

38. The system of claim 36, wherein the per-gene enrichment statistic is a contribution of the gene to a measure of similarity between the first gene set and the second gene set.

39. The system of claim 38, wherein the measure of similarity is a cosine similarity.

40. The system of claim 36, wherein the per-gene enrichment statistic is a partial cosine.

41. The system of claim 37, wherein using the per-gene enrichment statistics to identify the drug mechanism comprises identifying one or more genes contributing to a reversal of the genetic signature of the disease.

42. The system of claim 41, wherein identifying one or more genes contributing to a reversal of the genetic signature of the disease comprises identifying the one or more genes having a negative partial cosine.

43. The system of claim 41, wherein identifying one or more genes contributing to a reversal of the genetic signature of the disease comprises identifying the gene having the highest partial cosine.

44. The system of claim 36, wherein the library of gene expression signatures is a library or database of human cells responses to perturbations.

45. The system of claim 44, wherein the library of gene expression signatures comprises data from the National Institutes of Health (NIH) Library of Integrated Network-based Cellular Signatures (LINCS) database or the Broad Institute Connectivity Map (CMap) database.

46. The system of claim 36, wherein the subset of genes of the first gene set is a group of the top differentially expressed genes in the gene set.

47. The system of claim 36, wherein each of the gene expression signatures of the library corresponds to a candidate therapy causing changes in gene expression of cells.

48. The system of claim 36, wherein the instructions cause the processor to identify the first gene set comprising differentially expressed genes of metastatic cancer cells as compared to non-metastatic cancer cells.

* * * * *